United States Patent
Vachtesvanos et al.

(10) Patent No.: US 6,650,779 B2
(45) Date of Patent: Nov. 18, 2003

(54) METHOD AND APPARATUS FOR ANALYZING AN IMAGE TO DETECT AND IDENTIFY PATTERNS

(75) Inventors: George J. Vachtesvanos, Marietta, GA (US); Lewis J. Dorrity, Marietta, GA (US); Peng Wang, Atlanta, GA (US); Javier Echauz, Mayaguez, PR (US); Muid Mufti, Rawalpindi Cantt (PK)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/280,145

(22) Filed: Mar. 26, 1999

(65) Prior Publication Data

US 2002/0054694 A1 May 9, 2002

(51) Int. Cl.[7] .............................. G06K 9/46; G06K 9/68; G06K 9/62; H04N 7/18; G06E 1/00
(52) U.S. Cl. ...................... 382/228; 382/195; 382/218; 348/88; 348/92; 706/15
(58) Field of Search ................................ 382/190, 191, 382/192, 195, 218, 224, 111, 279, 156, 157, 228; 375/240.19; 706/15, 25; 348/88, 91, 92, 128

(56) References Cited

U.S. PATENT DOCUMENTS

| | | | | |
|---|---|---|---|---|
| 5,345,515 A | * | 9/1994 | Nishi et al. ................. | 382/111 |
| 5,548,120 A | * | 8/1996 | Parker et al. ............ | 250/341.7 |
| 5,774,177 A | * | 6/1998 | Lane ............................ | 348/88 |
| 5,815,198 A | * | 9/1998 | Vachtsevanos et al. ....... | 348/88 |
| 5,819,215 A | * | 10/1998 | Dobson et al. ............. | 704/230 |
| 5,841,890 A | * | 11/1998 | Kraske ........................ | 382/131 |
| 6,105,015 A | * | 8/2000 | Nguyen et al. ............... | 706/26 |
| 6,137,893 A | * | 10/2000 | Michael et al. ............. | 382/103 |
| 6,137,909 A | * | 10/2000 | Greineder et al. .......... | 382/190 |

OTHER PUBLICATIONS

Thyagarajan et al; "Fractal Scanning for Image Compression", IEEE Paper ISBN: 0–8186–2470–1, vol. 1, pp. 467–471.*

Sonlinh Phuvan, et al., Optoelectronic Fractal Scanning Technique For Wavelet Transform and Neural Net Pattern Classifiers Baltimore, Maryland, Jun. 7–11, 1992.

* cited by examiner

Primary Examiner—Mehrdad Dastouri
(74) Attorney, Agent, or Firm—Thomas, Kayden, Horstemeyer & Risley, LLP; Todd Deveau

(57) ABSTRACT

A method and apparatus is provided which analyzes an image of an object to detect and identify defects in the object utilizing multi-dimensional wavelet neural networks. "The present invention generates a signal representing part of the object, then extracts certain features of the signal. These features are then provided to a multidimensional neural network for classification, which indicates if the features correlate with a predetermined pattern. This process of analyzing the features to detect and identify predetermined patterns results in a robust fault detection and identification system which is computationally efficient and economical because of the learning element contained therein which lessens the need for human assistance."

42 Claims, 16 Drawing Sheets

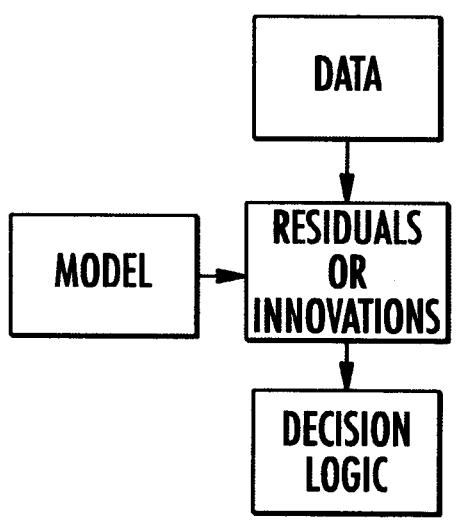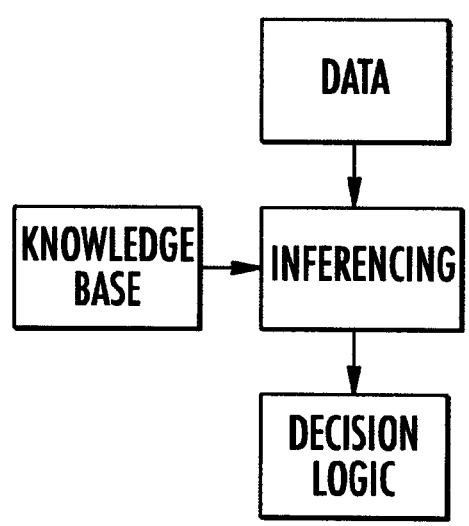
FIG. 1

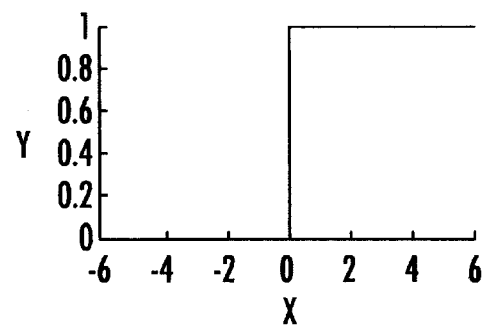
FIG. 2A
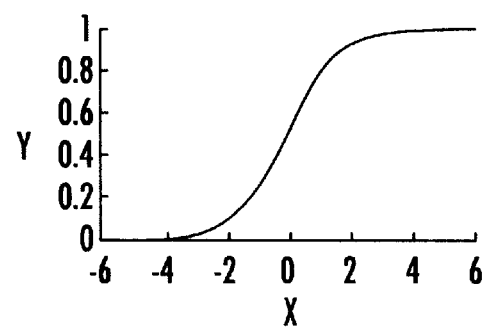
FIG. 2B
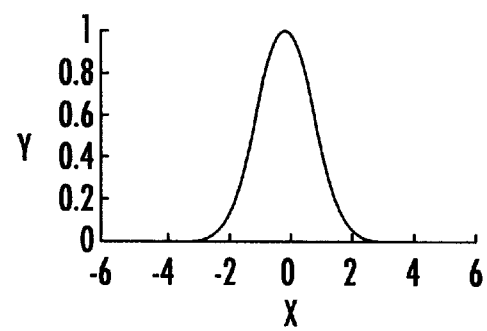
FIG. 2C
GAUSSIAN ACTIVATION FUNCTION
FIG. 3
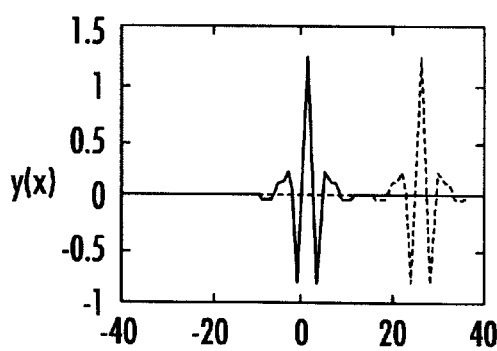
FIG. 4
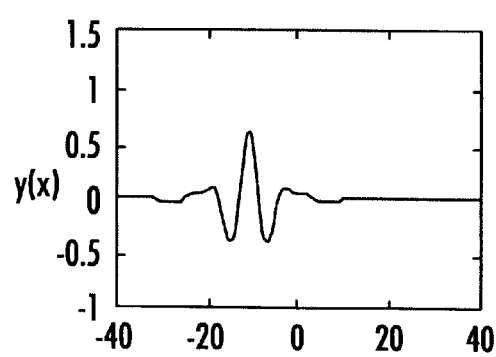

FIG. 7
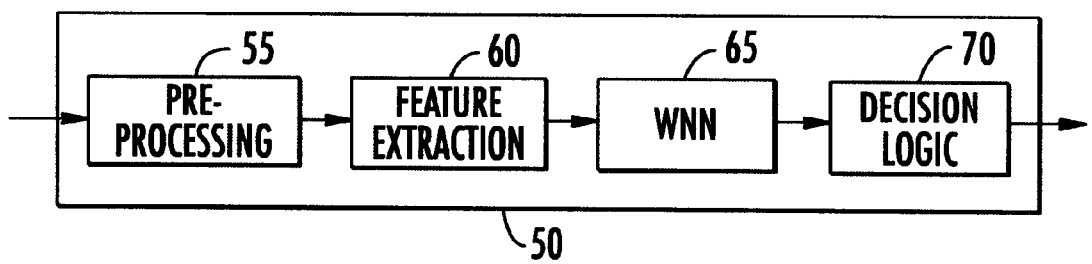
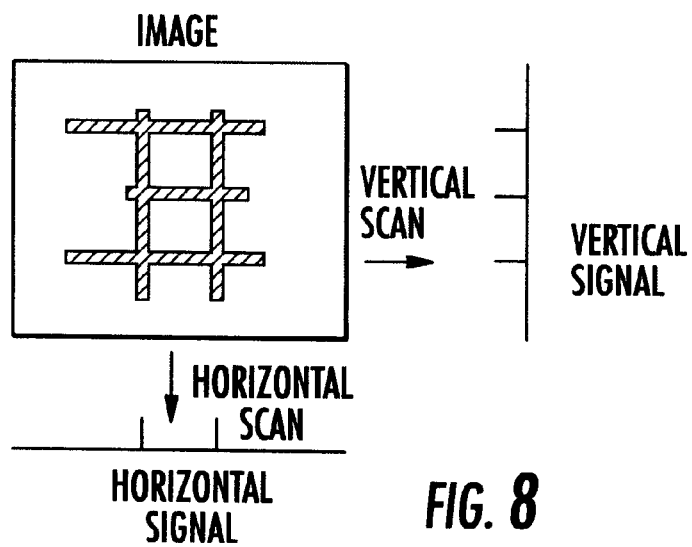
FIG. 8

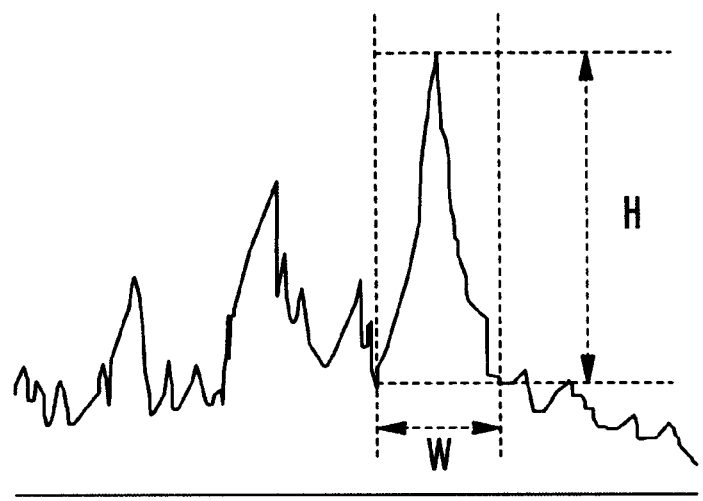
FIG. 9
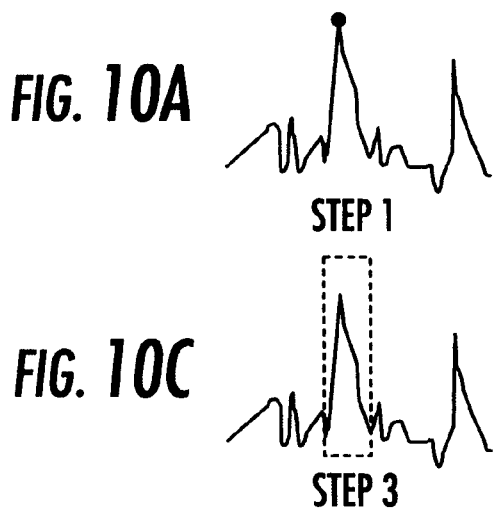
FIG. 10A  STEP 1
FIG. 10B  STEP 2
FIG. 10C  STEP 3
FIG. 10D  STEP 4

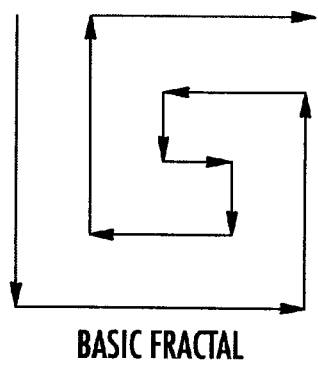
BASIC FRACTAL
FIG. 21A
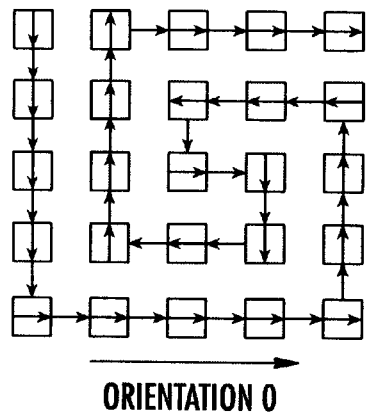
ORIENTATION 0
FIG. 21B
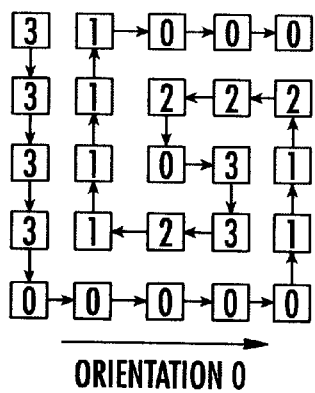
ORIENTATION 0
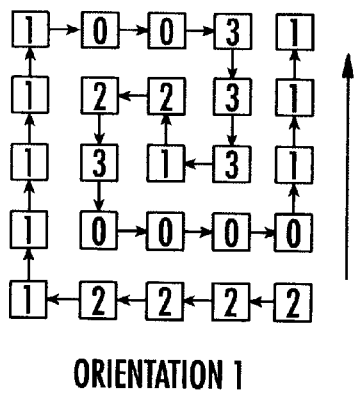
ORIENTATION 1
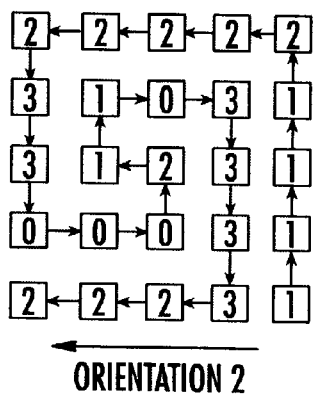
ORIENTATION 2
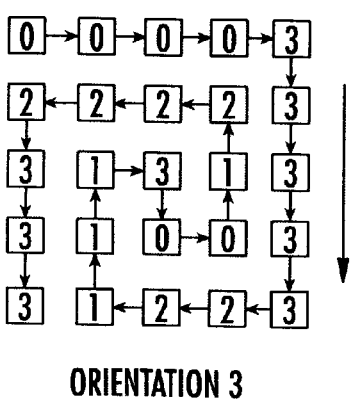
ORIENTATION 3
FIG. 22

METHOD AND APPARATUS FOR ANALYZING AN IMAGE TO DETECT AND IDENTIFY PATTERNS

BACKGROUND OF THE INVENTION

1. Technical Field of the Invention

The present invention relates to a method and apparatus for detecting and classifying patterns and, amongst other things to a method and apparatus which utilizes multi-dimensional wavelet neural networks to detect and classify patterns.

2. Background Art

Current trends in industrial and manufacturing automation have placed an increased emphasis on the need for quality and reliability, both in the process control and product characterization areas. As the technologies are becoming more complicated, the production of virtually defect free products by reliable processes is becoming vital. Automatic control systems are becoming more complex as they are called upon to regulate critical dynamic systems and the associated control algorithms and control actuators entail a greater degree of sophistication. Consequently, there is a growing demand for fault tolerance, which can be achieved by improving the Fault Detection and Identification (FDI) concepts. FDI is of interest in a wide variety of applications such as control systems, image analysis, analysis of radar signals, smart sensors, texture analysis, medicine, industry, etc.

FDI algorithms generally consist of two portions, a detection portion and an classification portion. Detection is the process of deciding whether any one of a number of anticipated events, e.g. faults or defects, has occurred. Once the presence of an anticipated event has been established, classification distinguishes which particular anticipated event, e.g. defect, has occurred. There are a number of systems where traditional FDI techniques are not applicable due to the unavailability of analytic models. FDI becomes more difficult when there is a large variation in signal time constants. A high degree of system interdependencies, process and measurement noise, large-grain uncertainty and randomness make detection of anticipated events even more challenging.

Analysis of signals in either the time or frequency domain generally is not sufficient to capture faults that occur over a wide band of frequencies. Analysis of faults in pattern recognition applications should be localized in both the time and frequency domains for each input signal.

Over the last two decades, basic research in FDI has gained increased attention, mainly due to trends in automation, the need to address complex tasks, and the corresponding demand for higher availability and security of the control systems. However, a strong impetus has also come from the side of modem control theory that has brought forth powerful techniques in mathematical modeling, state estimation and parameter identification.

In general, FDI schemes can be classified broadly as: (1) model based FDI techniques; and (2) knowledge based FDI techniques. Model based techniques (analytic) generally use information about state variables from the model of the system to predict the future values. A disparity between the actual values and the predicted values suggests a possible fault. This is a very robust approach to FDI for systems where accurate models are available. However this approach has difficulty where accurate or complete models of the system are unavailable.

Model-based FDI techniques have been thoroughly tested and verified to perform satisfactorily in many applications. Based upon the methods of using the model, various approaches have been developed. For example, innovation-based techniques, such as Generalized Likelihood Ratio, are used for linear stochastic systems. This technique requires N+1 hypothesis testing: $H_i$ for the occurrence of fault i, i=1, . . . , N, and $H_o$ for no failure. The failure decision is based upon the maximum likelihood ratio of the conditional probabilities for $H_i$ and $H_o$. A technique known as the Failure Sensitive Filters technique employs a class of filters wherein the primary criterion for the choice of the filter is that the effects of certain faults are accentuated in the filter residue. However, it is not always possible to design a filter that is sensitive only to a particular fault. Furthermore, a performance trade off is inherent in this method. For, as the sensitivity of the filter to new data is increased, by effectively increasing the bandwidth of the filter, the system becomes more sensitive to sensor noise and the performance of the detection algorithm in no-failure conditions degrades.

Another technique known as the Multiple Hypothesis Filter Detectors technique uses a bank of filters (one for each fault mode) and each filter is used to calculate the conditional probability that each failure mode has occurred. This technique generally is not very popular due to its level of complexity, which increases exponentially as the system expands. Since the complexity of the technique increases the processing time required, the processing time also increases exponentially with the complexity of the technique.

The Parity Space Approach exploits the inconsistency of data (due to failure) coming from different sources of the system. The Direct Redundancy or Hardware Redundancy technique uses the instantaneous values of different sensors while the Temporal Redundancy technique uses a dynamic relationship between sensor outputs and actuator inputs over a period of time. The Hardware Redundancy technique is simple and easy to apply. However, it requires multiple sensors for each variable. Another drawback of this technique is that it works on the assumption that only one sensor fails at a time (in a three sensor arrangement). Analytic Redundancy uses data from sensors representing different parameters of the system that can be mathematically related by the model or part of the model.

With the availability of mathematical and computational tools, the trend in FDI research has shifted toward analytical (i.e., functional) rather than physical redundancy. This implies that the inherent redundancy contained in the dynamic relationships among the system inputs and measured outputs is exploited for FDI. In such approaches, one makes use of a mathematical model of the system or models describing certain modules of the overall system.

The known techniques described above utilize a model of the system (or part of the system) for fault analysis. These techniques work satisfactorily as long as the model characteristics approximate the actual system. However, their performance degrades rapidly if the model does not accurately represent the actual system. Unfortunately, accurate models are not available for most systems. There is a growing potential for using knowledge-based models and algorithms instead of analytic ones. This approach is, of course, the only one available in cases where analytic models are not available. A comparison of a model-based technique and a knowledge-based technique is shown in FIG. 1. It can be seen in FIG. 1 that the knowledge base replaces the model in the overall architecture. This knowledge-based approach has created a new dimension of possible fault diagnosis techniques for complex processes with incomplete process knowledge. Whereas the analytic methods use quantitative analytical models, the expert systems approach makes use of qualitative models based on the available knowledge of the system. Although the intelligent FDI techniques do not require an accurate analytic model, they are restricted to identification of only predetermined defects. This is, however, acceptable in many cases as the fault modes in many applications are already known.

From the perspective of product characterization, one aspect of quality is perceived as a defect-free final product. Product inspection and defect classification is one of the key issues in the manufacturing arena, where defect classification is a pattern recognition problem. Manual inspection or traditional signal processing have proven to be inadequate in many applications. This is due to the presence of a high degree of uncertainty and complexity in these systems. Intelligent processing tools like fuzzy logic, neural networks and intelligent optimization techniques are currently being used which accommodate large grain uncertainty while utilizing all the information about the system when the information from analytic models of the system is not adequate. This gives intelligent FDI schemes an advantage over conventional FDI techniques, which rely primarily on analytic models. However, heretofore intelligent FDI systems have analyzed signals in either the time or frequency domain exclusively. Due to the wide range of time constants, analysis in the frequency domain alone would mask the sudden bursts of high frequency signals. Further, unless the frequency domain resolution is very fine, slowly varying fault features can be masked in a signal akin to a DC bias. Likewise, analysis in the time domain would not reflect the periodicity of the features. Hence, analysis only in either the frequency or time domain generally is not sufficient to capture features that are spread over a wide band of frequencies.

Most of the intelligent techniques being used today employ a learning mechanism (on-line or off-line) which uses information obtained from an expert, historical data, extrinsic conditions, etc. The learning procedure, in most cases, is cast as an optimization problem which adjusts the parameters of the detection algorithm, modifies the knowledge-base, initiates mode switching, etc. For example, it is known to use learning to determine the optimum weights for aggregation of information from different sources for vibration monitoring. Neural-net based FDI techniques are known which use learning to adjust the weights of individual neurons. Fuzzy Associative Memories (FAMs) are known which employ learning to design an inferencing hypercube.

The fault identification is the classification of faults into different categories. It may be viewed as a mapping from a feature space to a decision space. One well known fuzzy classification routine is the Fuzzy C-Means (FCM) algorithm derived from its crisp version called ISODATA. Consider the partitioning of the set $X=\{x_1, x_2, \ldots, x_n\}$ into c-partitions, $c \in N$. FCM assigns a degree of association $\mu_{ik}$ of the kth feature with the ith partition (fault mode in our case). For the cluster center $v_i$ of the ith cluster, FCM estimates $\mu_{ik}$ as follows $$\min z = \sum_{i=1}^{c} \sum_{k=1}^{n} (\mu_{ik})^m \|X_k - V_i\| \qquad \text{Equation 1}$$

These types of approaches work on the assumption that the fuzzy classes are fully understood by the user and that there exists sufficient knowledge of the associated features. They do not allow the classes to be self generated or evolved over time. Hence, they lack the element of learning that would enable the system to work independently without user assistance.

The defect detection problem is in fact a problem of classifying features of the signal representative of characteristics of the product into different categories. It may be viewed as a mapping from the feature space to a decision space where detection and classification can occur. Further, similarity measures combining vague features with known patterns have been used for classification. These approaches work on the assumption that the fuzzy classes are fully understood by the user and there exists sufficient knowledge of the associated features. They do not allow the classes to be self-generated or evolving over time. Hence, they lack the element of learning that would enable the system to work independently without user assistance.

A multi-level architecture for feature classification based on fuzzy logic has been utilized as one approach. Other popular methods for classification use a fuzzy rule-base, fuzzy decision hypercube, fuzzy relational matrix, and fuzzy associative memories (FAM). All these techniques rely upon the user to provide the expert knowledge for the inference engine, which is somewhat problematic, as the defect in a single class will vary in and of themselves. Additionally, the generation of a fuzzy decision hypercube or FAM is not very simple for most in industrial applications.

Many intelligent techniques employ a learning mechanism (unsupervised or supervised) which uses information from an expert, historical data, extrinsic conditions, etc. The learning procedure, in most cases, is cast as an optimization problem which adjusts the parameters of the detection algorithm, modifies the knowledge-base, initiates mode switching, etc. One approach uses learning to determine the optimum weights for aggregation of information from different sources for vibration monitoring. Neural net based FDI techniques use learning to adjust the weights of individual neurons while Fuzzy Associative Memories employ learning to design the inferencing hypercube.

Feature analysis is used for detection and classification of operating modes of the system under observation. Possible operating modes may include, stable condition, subnormal operation, or failure modes. The task of a feature analysis algorithm is to differentiate between a system failure and a functional failure. A system failure is a degradation of performance of the hardware of the system while a functional failure refers to a condition of the system state variables resulting in an unwanted operating mode such as instability. Many functional failures may eventually lead to a system failure.

Product characterization is another very important application area of feature analysis algorithms. This application domain includes product quality inspection, texture classification, signal and image classification, and similar applications.

Traditionally, model-based techniques have been used for feature extraction. These techniques rely solely on an accurate model of the system. Failure sensitive filters and multiple hypotheses filter detectors aim at classifying abnormal system behavior using system models. Model-based techniques perform satisfactorily as long as the model characteristics are close to the actual system. However, performance degrades' rapidly if the model does not closely represent the actual system. Unfortunately, accurate models are not available for most systems. Another approach utilizes knowledge-based models instead of analytic ones.

Knowledge based feature extraction systems have the capability of including a wider range of information sources as input-output data, heuristics, and other iterative methodologies.

With the availability of powerful computing platforms, feature processing has become an important part of many applications utilizing intelligent processing tools like fuzzy logic and neural networks. The terms "failure", "fault" and "defect" are employed to designate an abnormal system state and are context dependent, the term "failure" suggests a generic condition whereas "fault" and "defect" are used to signify an off normal condition of a dynamic (sensor, actuator, etc.) and a static (product characterization) system state, respectively.

Another very important feature in the industrial applicability of FDI systems is that of computational overhead, or more processing speed. That is, the greater the processing overhead required, the slower the speed of the operation of the FDI system. In industrial processes, it is the speed of the process that is the benchmark at which the FDI system must function. However, the increase in the computational speed of the FDI should not come at the price of lost accuracy, which would defeat the purpose of the installation of the FDI system.

One of the more promising techniques for FDI systems is the utilization of wavelet neural networks. A neural network is composed of multiple layers of interconnected nodes with an activation function in each node and weights on the edges or arcs connecting the nodes of the network. The output of each node is a nonlinear function of all its inputs and the network represents an expansion of the unknown nonlinear relationship between inputs, x, and outputs, F (or y), into a space spanned by the functions represented by the activation functions of the network's nodes. Learning is viewed as synthesizing an approximation of a multidimensional function, over a space spanned by the activation functions $\phi(x)$, i=1, 2, . . . , m, i.e.

$$F(x) = \sum_{i=1}^{m} c_i \phi_i(x) \qquad \text{Equation 2}$$

The approximation error is minimized by adjusting the activation function and network parameters using empirical (experimental) data. Two types of activation functions are commonly used: global and local. Global activation functions are active over a large range of input values and provide a global approximation to the empirical data. Local activation functions are active only in the immediate vicinity of the given input value. Typical global activation functions, the linear threshold and the sigmoid function, are shown in FIGS. 2a and 2b. The Gaussian for radial basis function networks is a typical example of a local activation function is shown in FIG. 2c. The functions which can be computed by a Back Propagation Network (BPN) with one hidden layer having m nodes constitute the set $S_m$ defined by:

$$S_m \equiv \left\{ f(x) : f(x) = \sum_{i=1}^{m} c_i \phi(xw_i + \theta_i), w_i \in R^d, c_i, \theta_i \in R \right\} \qquad \text{Equation 3}$$

where f(x) is the sigmoid function and $m_i$, $c_i$, and $\theta_1$, are adjustable parameters. The activation function in Radial Basis Function Networks (RBFN) is local in character and given, in general, for the ith node by:

$$\phi_i(x) = h(\|x - x_i\|) \qquad \text{Equation 4}$$

If h is Gaussian, $$\phi_i(x) = \left( \frac{-\|x - x_i\|}{2\sigma_i^2} \right) \text{ if } x \in R \qquad \text{Equation 5}$$

$$\phi_i(x) = \frac{|W_i|}{\pi^{d/2}} \exp\left(-\frac{1}{2}(x-x_i)^T W_i^2 (x-x_i)\right) \text{ if } x \in R \qquad \text{Equation 6}$$

where $\delta_i$ is the standard deviation for the one-dimensional case and $W_i$ the dxd weight matrix formed by reciprocals of the covariance of the d-dimensional case. Adaptation and learning with global approximations is a slow process since each network node influences the output over a large range of input values and all activation functions overlap over a large range of input values, thus interacting with each other. Convergence of BPNs is not guaranteed due to the nonlinear nature of the optimization problem. Moreover, global approximation networks provide a value for the output over the whole range of input values independently of the availability or density of training data in given ranges of input values. Such a property could lead to large extrapolation errors without warning. RBFNs avoid large extrapolation errors, have less convergence problems than BPNs, and are trained faster and adapt easily to new data since they require changes in only a small part of the net.

It is well known that functions can be represented as a weighted sum of orthogonal basis functions. Such expansions can be easily represented as neural nets by having the selected basis functions as activation functions in each node, and the coefficients of the expansion as the weights on each output edge. Several classical orthogonal functions, such as sinusoids and Walsh functions for example, are global approximations and suffer, therefore, from the disadvantages of approximation using global functions, i.e. potentially large extrapolation errors. What is needed is a set of basis functions that are local and orthogonal. A special class of functions, known as wavelets, possess good localization properties while also being simple orthonormal bases. Thus, they may be employed as the activation functions of a neural network known as the Wavelet Neural Network (WNN). WNNs possess a unique attribute, in addition to forming an orthogonal or quasi-orthogonal basis they are also capable of explicitly representing the behavior of a function at various resolutions of input variables.

Neural network design has been traditionally plagued by problems of arbitrariness, e.g. the number of nodes and hidden layers. The design of neural nets can be systematized and the arbitrariness may be removed by using activation functions that are naturally orthogonal and have local receptive fields. Thus, if the properties, the training of a neural network could be completely localized, while the number of hidden nodes would be directly determined by the added accuracy offered by a new node. This can be seen by considering a function F(x) which is assumed to be continuous in the range [0, 1]. Let $\phi$; (x), i=1,2, . . . , $\infty$ be an orthonormal set of continuous functions in [0, 1]. Then, F(x) possesses a unique $L^2$ approximation of the form:

$$F(C, x) = \sum_{i=1}^{n} c_k \phi_k(x) \qquad \text{Equation 7}$$

where the elements of the vector of coefficients C=[$C_1$, $C_2$, . . . , $C_N$]$^T$ are given by the projection of F(x) onto each basis function, that is $$c_k = \int_0^1 F(x)\phi(x)dx \qquad \text{Equation 8}$$

A reasonable performance (interpolation) metric is the mean-squares error, i.e.

$$e_k^2 = \int_0^1 \left[F(x) - \sum_{i=1}^{K} c_k \phi_k(x)\right] dx = \sum_{k=K+1}^{\infty} c_k^2 \qquad \text{Equation 9}$$

As the mean-squared error decreases, by increasing the number of terms K, the approximation improves. Furthermore, the larger the value of the coefficient, $C_k$ the greater the contribution of the corresponding basis function $\phi^k(x)$, in the approximating function. This observation provides a formal criterion for picking the most important activation function in each hidden unit of a network.

In addition to "good" neural net design approaches, another important ingredient in the approximation problem is the multiresolution property. Consider, for example, the case of training data that are not uniformly distributed in the input space, i.e., data are sparse in some regions and dense in others. Approximating such data at a single coarse resolution may not bring out the fine details. A single fine resolution brings out the details, but no general picture may emerge. This tradeoff between the ability to capture fine detail and good generalization may be solved by learning at multiple resolutions. A higher resolution of the input space may be used if data are dense and lower resolution where they are sparse.

A function F(x) may be expressed by its multiresolution components at L scales by $$F_L(x) = \sum_{m=1}^{L} f_m(x) \qquad \text{Equation 10}$$

where, the component at the m-th scale, $f_m(x)$, is given by $$f_m(x) = \sum_{k=1}^{K} c_{mk} \phi_{mk}(x) \qquad \text{Equation 11}$$

The basis functions $\phi^{mk}(x)$ are all defined at scale m. If m=0 defines the lowest scale (finest resolution of input data) and m=L the highest, the neural network is trained to learn the mapping between inputs and output at the coarsest resolution first; then, the network is trained to learn the added detail as one moves from a coarser to a finer level of resolution. The error in the approximation at each resolution is given by $$e_m^2 = \int_0^1 \left[f_m(x) - \sum_{k=1}^{K} c_{mk} \phi_{mk}(x)\right]^2 dx \qquad \text{Equation 12}$$

Orthogonal wavelets generate such a multiresolution representation.

A family of wavelets is derived from the translations and dilations of a single function. If $\psi(x)$ is the starting (mother) function, to be called a wavelet, the members of the family are given by $$\frac{1}{\sqrt{s}} \psi\left(\frac{x-u}{s}\right) \text{ for } (s, u) \in R^2 \qquad \text{Equation 13}$$

that is they are indexed by two labels (parameters) s and u, with s indicating the dilation and u the translation of the base wavelet, $\psi(x)$. The translation and dilation of the Battle-Lemarie wavelet is shown in FIGS. 3 and 4.

An important factor in the formulation and design of neural networks with wavelets as basis functions, is the multiresolution representation of functions using wavelets. It provides the essential framework for the completely localized and hierarchical training afforded by Wavelet Neural Networks. Consider a continuous, square-integrable function, F(x), with $F_m$, $(x) \equiv A_m F(x)$ denoting the approximation of F(x) at the resolution m, where $2^m$ is the sampling interval, that is, the interval between two consecutive sampled values used in the approximation. Then, $2^{-m}$ is the number of sampled values per unit length of input space. Consequently, as m increases, the number of samples per unit length decreases and the approximation $F_m(x)$ becomes coarser. It has been shown that there exists a unique function, $\phi(x)$, called a scaling function, such that for all $m \in Z$, the family of functions resulting from the dilation and translation of $\phi(x)$, that is:

$$\phi_{mk}(x) = \sqrt{2^{-m}} \phi(2^{-m}x - k)(m,k) \in Z^2 \qquad \text{Equation 14}$$

constitutes an unconditional orthonormal basis. With this basis function, $F_m(x)$ is given by $$F_m(x) \equiv A_m F(x) = \sum_{k=-\infty}^{+\infty} a_{mk} \phi_{mk}(x) \qquad \text{Equation 15}$$

and the coefficients $a_{mk}$ are projections of F(x) onto the orthonormal basis function, that is, $$a_{mk} = \int_{-\infty}^{\infty} F(x) \phi_{mk}(x) dx \qquad \text{Equation 16}$$

At various resolutions, any $F(x) \in L^2(R)$ can be expanded into a set of orthonormal wavelets, that is, $$F(x) = \sum_{m=-\infty}^{\infty} \sum_{k=-\infty}^{\infty} d_{mk} \psi_{mk}(x) \qquad \text{Equation 17}$$

The above equation is known as the wavelet decomposition of a square-integrable function, and provides the theoretical framework for the design of Wavelet Neural Networks. The coefficients $d_{mk}$ are the projects of F(x) on the basis functions $\psi_{mk}(x)$. It can be shown that the approximation of F(x) at scale (m−1) is equal to $$F_{m-1}(x) = F_m(x) + \sum_{k=-\infty}^{\infty} d_{mk} \psi_{mk}(x) \qquad \text{Equation 18}$$

This last equation summarizes the hierarchical, multiresolution representation of functions offered by the wavelet decomposition.

From a practical perspective, given a sequence of discrete samples of F(x), resulting from physical measurements, $$F_0(x) = \sum_{k=-\infty}^{\infty} a_{0k}\phi_{0k}(x) \qquad \text{Equation 19}$$

the recursive decomposition of the discrete sequence of samples is characterized by $$A_{m-1}F(x) = \sum_{k \in Z} a_{mk}\phi_{mk} + \sum_{k \in Z} d_{mk}\psi_{mk}(x) \qquad \text{Equation 20}$$

with the coefficients of the decomposition given by $$a_m = Ha_{m-1} d_m = Ga_{m-1} \qquad \text{Equation 21}$$

Filters H and G are defined in such a way that the impulse responses are given by $$h_k = \int_{-\infty}^{\infty} \phi_{0k}(x)\phi_{1k}(x)dx \qquad \text{Equation 22}$$

$$g_k = \int_{-\infty}^{\infty} \phi_{0k}(x)\psi_{1k}(x)dx$$

The developments above are based on infinite length sequences of sampled values. Finite sequences result in "end effects" which may be addressed by considering a mirror image of the trend beyond its end points or by defining appropriate H and G filters.

The principal benefit from the wavelet decomposition is the localized characterization of a continuous or discrete function in the input space, and wave number (or frequency, or scale). The input-frequency localization of wavelets at various translations and dilations is shown in FIG. 5. Each rectangle indicates the input space and scale space localization of the corresponding wavelet. The size of each rectangle is determined by the standard deviation of the wavelet and its Fourier transform. The area of each rectangle is constant, indicating that as the frequency range increases, the input range decreases, as governed by the uncertainty principle. The information contained in the input and frequency range covered by each wavelet or scaling function is captured by the coefficients dmk and ak, respectively. Consider coefficient d2, 23 in the grid of FIG. 6. The value of d2, 33 measures the content of the original signal in terms of the wavelet at the 2-nd dilation, when the input takes on values in the range [33-q, 33+q]. In other words, it measures the content of the original signal in the frequency range corresponding to the frequencies allowed at scale 2, and in the input range [33-q, 33+q]. This range is indicated by the encircled points in the figure. Here q is assumed to be 2 units.

A major challenge for wavelet theorists has been to extend the success they have had on one-dimensional signals to more dimensions. This is especially important for real world defect identification or pattern recognition problems, as the number of different features of the image or signals created from the image that are indicative of a defect or pattern are numerous, and no single feature is generally sufficient to be relied upon to signify the existence of a defect.

BRIEF SUMMARY OF THE INVENTION

In accordance with the present invention, a method and apparatus is provided which analyzes an image of an object to detect and identify defects in the object. The method and apparatus generate a signal representing at least part of the object. Certain features of the signal are extracted and then provided to a multi-dimensional neural network for classification.

In one embodiment the present invention comprises an apparatus for analyzing a 2-D representation of an object. The apparatus comprises at least one sensor disposed to capture a 2-D representation, a memory that stores at least a portion of the 2-D representation; and a processor that derives a signal from the 2-D representation, that generates a plurality of feature values and that provides the feature values to a multi-dimensional wavelet neural network which provides a classification output indicative of whether the representation comprises a predetermined pattern.

In another embodiment the present invention comprises a method for pattern recognition, comprising generating a 2-D digital representation of at least part of an object, extracting feature values from the 2-D digital representation, providing the feature values to a multi-dimensional wavelet neural network; and providing a classification output indicative of a predetermined pattern if the feature values are indicative of a predetermined pattern.

In a further embodiment the invention comprises a computer readable medium containing instructions for a computer comprising means for instructing the computer to read at least a portion of a 2-D digital image, means for instructing the computer to generate a feature vector, means for instructing the computer to provide the feature vector to a multi-dimensional wavelet neural network; and means for instructing the computer to provide a classification output indicative of a predetermined pattern from the multi-dimensional neural network if the feature values are indicative of a predetermined pattern.

In an additional embodiment the present invention comprises an apparatus for pattern recognition. The apparatus comprises an input that receives a 2-D representation of at least part of an object, a memory that stores at least a portion of the 2-D representation; and a processor that generates a plurality of feature values representing features of said at least one signal and that provides the feature values to a perceptron neural network comprising a plurality of neurons each defined by the function $\psi_{a,b} = \sqrt{|diag(a)|}\psi(diag(a)(x-b))$ where x is a vector comprising said feature values, a is a squashing matrix for the neuron and b is the translation vector for that neuron. The perceptron neural network provides a classification output indicative of whether the representation contains a predetermined pattern.

Accordingly, it is an object of the present invention to provide a robust fault detection and identification system.

It is another object of the present invention to provide a fault detection and identification system which is computationally efficient.

It is yet another object of the present invention to provide a fault detection and identification system which can be incorporated as part of a manufacturing line for real time detection and identification of defects occurring in an object being manufactured and for controlling the manufacturing process to improve the production quality of the object being manufactured.

It is yet another object of the present invention to provide an intelligent fault detection and identification system which can be incorporated into a textile fabric manufacturing process for detecting defects in fabric being manufactured and for controlling the manufacturing process to eliminate or minimize defects in the fabric.

It is yet another object of the present invention to provide a robust fault detection and identification system which is economical.

These and other objects of the present invention are depicted and described in the following description, drawings and claims.

BRIEF DESCRIPTION OF THE DRAWINGS

FIG. 1 depicts a block diagram comparing model based FDI techniques to knowledge based FDI techniques.

FIG. 2a depicts a typical global linear threshold function utilize in a neural network.

FIG. 2b depicts a typical global sigmoid function utilize in a neural network.

FIG. 2c depicts a typical global gaussian activation function utilize in a neural network.

FIG. 3 depicts the translation of a Battle-Lemarie wavelet.

FIG. 4 depicts the dilation of a Battle-Lemarie wavelet.

FIG. 7 is a block diagram of the pattern detection system of the present invention.

FIG. 8 is a diagram of the presently preferred scanning method utilized as part of the preprocessing module according to the present invention.

FIG. 9 is a diagram of the presently preferred feature extraction process according to the present invention.

FIGS. 10a–10d are graphical representations of the individual steps of the presently preferred feature extraction process of FIG. 9 according to the present invention.

FIG. 21a illustrates a preferred basic fractal scanning pattern of the present invention.

FIG. 21b illustrates a 5×5 dimension of the fractal scanning pattern of FIG. 21a.

FIG. 22 illustrates basic orientation of different fractals.

DETAILED DESCRIPTION OF THE INVENTION

Figure 5:
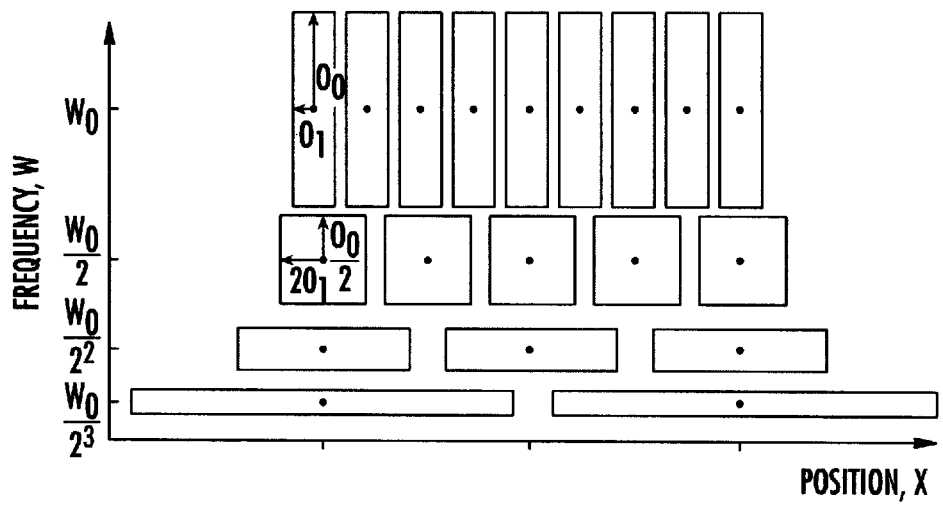
FIG. 5 depicts the input-frequency localization of wavelet functions at various translations and dilations.
Figure 6:
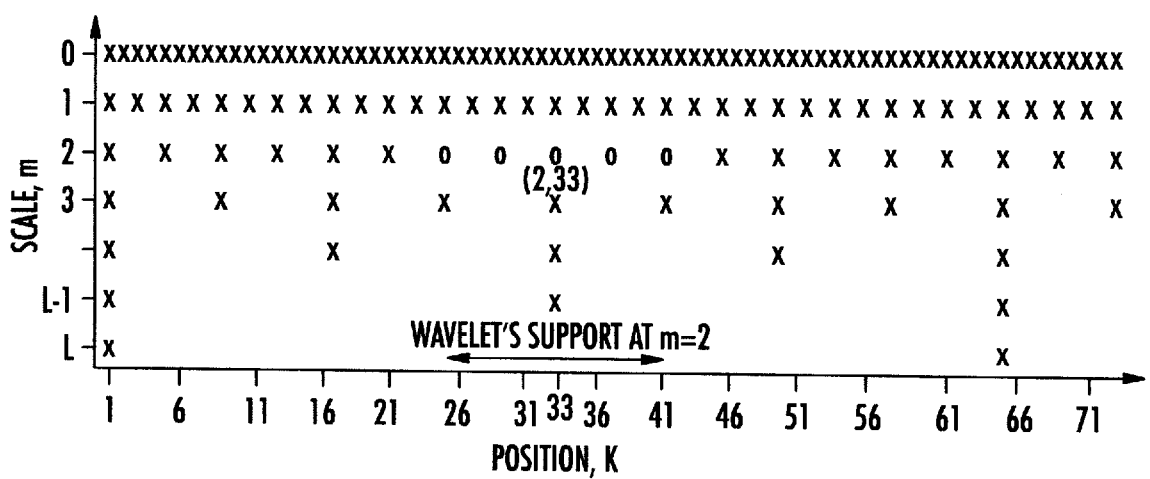
FIG. 6 depicts the input frequency for a particular wavelet function for a particular coefficient.

In a preferred embodiment the present invention includes a pattern identification system which is part of an FDI system utilized in an industrial process. The pattern identification determines the existence of predetermined, or preprogrammed, patterns. Upon detecting the existence of one of the predetermined patterns the pattern identification system classifies the detected pattern as one of the predetermined patterns allowing correction of the industrial process or maintenance of records relating to the process.

A. Pattern Identification System

The pattern identification system of the present invention is preferably utilized to both detect and classify defects. Referring to FIG. 7, pattern identification system 50 is preferably divided into the following identification task a preprocessing module 55, a feature extraction module 60, a multi-dimensional wavelet neural network (WNN) module 65, and a decision logic module 70. Preprocessing module 55 is employed to reduce the search space allocated to the feature extraction module 60 and to enhance the target image compared to noise or clutter typically encountered in a raw image, i.e. to reduce the signal to noise ratio of the signal to be operated upon by the feature extraction module 60. The feature extraction module 60 estimates the best features that distinguish the target (defect) from a normal image or other defects. The WNN is used as the pattern identifier that exploits the features and decides upon which defect category the current defect belongs to. Further, the output of the WNN module 65 may be utilized to perform the classification functions either within the WNN module 65 or in another module, such as decision logic module 70. Decision logic module 70 is designed to resolve conflicts for the purposes of classification based upon the heuristic knowledge, i.e. knowledge derived from experienced operators, raw data and data from other modules such as the feature extractor and the WNN. Its task is to aggregate or fuse the evidence, account for incomplete, and resolve conflicts. It is set as an expert system using fuzzy logic and Dempter-Shafer theory. Decision logic module 70 is preferably utilized to classify the pattern detected by the pattern identification system 50 where the output of the WNN 65 is indicative of more than one known pattern. The decision logic module 70 will make the determination as to which of the known patterns is more likely based upon the outputs of the preprocessing module 55 and feature extraction module 60. These procedures are preferably all implemented as discrete software programs however, the procedures may be integrated as a single software program. Nonetheless, it should be pointed out that there is an important real-time constraint for the program(s) so as to reduce identification time. This must be done without sacrificing identification accuracy.

1. Preprocessing

The parameters of preprocessing module 55 are set in conjunction with those of feature extraction module 60 and has the objectives of reducing the search space to ease the computational burden of feature extraction, enhancing the real signal and to improving the quality of feature extraction. Preprocessing module 55 can operate on either an image in 2-dimensional space or a 1-dimensional signal, depending on the features to be extracted as well as the processing time requirements. There are a number of techniques available that can be utilized as functions for the preprocessing module 55. These include projection techniques, for instance, horizontal, vertical, or diagonal projections; enhancement techniques, for example, histograms, spectrum, and cepstrum based enhancements; filtering techniques, including low-pass, high-pass, band-pass, morphological filtering; segmentation techniques, such as manual, binary, outline-based segmentation, and similar processes the goal of which is to improve the signal to noise ratio of the signal or image for the feature extraction module 60. The preprocessing techniques can also be concatenated so as to achieve better processing results. The presently preferred preprocessing module can be utilized to perform the defect detection task as well by utilizing the appropriate filters to remove portions of the signal that are outside of the parameters that may signify a defect, e.g. a low pass filter if it is determined that the high frequency signals are noise and not indicative of the defect. The actual scope of the parameters is a function of degree of certainty of the system designer and the need for processing speed of the system. That is, if the designer is uncertain, more signals can be allowed to pass the filters and a more accurate WNN can be utilized to determine the existence of a defect.

In many FDI systems where the present pattern recognition system can be utilized, e.g. textile processes, the computational time allowed is very low as the processes that are being examined run at relatively high speeds. In these textile processing applications the reduction of the search space appears to be one of the highest priorities. A projection method is preferred which is optimized to the nature and uniqueness of fabric defects. Fabric defects are mostly oriented horizontally or vertically, i.e., either in the filling or the warp direction. This defect orientation is determined by the way in which fabrics are woven. Since only line type of information is important, time-consuming 2-D identification is not necessary unless defect details must be identified to an extreme detail. Thus, a method is utilized for projecting the 2-D image horizontally and vertically into two 1-D signals, respectively. The horizontal projection entails a vertical scan while the vertical projection is called horizontal scan and produces horizontal signals. This projection is illustrated in FIG. 8. By projection, more specifically we mean that the average of all pixel values along a specific direction is computed and this average value (a point) is representative of all the pixels (a line). Mathematically, this type of projection can be expressed as follows:

(1) vertical signal: $P_h(i, \cdot) = \sum_{i=1}^{n} A(i, j)/n$  Equation 23

(2) horizontal signal: $P_V(\cdot, j) = \sum_{i=1}^{m} A(i, j)/m$  Equation 24 where A(i,j) is the image matrix and i=1, ..., n and j=1, ..., m.

If the projected signals are relatively weak compared to noise, 2-D preprocessing could be helpful when time is not a critical factor. It should be noted that the prefix "pre-" in 2-D preprocessing means "before" the projections are carried out. After the projections, the "pre-" in 1-D preprocessing is viewed as "before" feature extraction, actually indicating "post-" processing for the projections. These 1-D processing approaches cater to the feature extractor though they are, in principle, the same as 2-D preprocessing methods for the projections. Possible choices of 1-D preprocessing tools include high-pass filters, median filters, and even wavelet filters or filter banks. The feature extractor should be able to benefit from these filters in reducing or even eliminating possible gradient calculations. Moreover, defect probabilities are also a factor in determining which preprocessing techniques ought to be employed. The smaller these probabilities, the longer the time expenditure.

2. Feature Extraction

The objective of feature extraction module 60 is to determine and extract appropriate features for the defect classification task. An additional objective is to reduce the search space and to speed up the computation of the WNN.

Returning to the example of fabric defects, a windowing operation is applied to the 1-D signals in order to reduce the search space and facilitate the selection of appropriate features prior to feature selection. This procedure presumes the fact that the number of defects on a single image is limited. Therefore, the useful or target signal accounts for only part of the 1-D signal while the remaining portion of the signal is noise. As shown in FIG. 9, a window is applied on a signal so as to narrow the signal space, thus reducing the signal range into a windowed portion where the probability of the existence of the "true" or target signal, representing the pattern or defect, is maximum.

The window can be of fixed or variable width. The presently preferred feature selection module 60 utilizes an adaptive windowing technique that creates a variable window via the calculation of gradients, however other variable width windows or fixed width windows can be utilized by the present invention without departing from the scope thereof. The adaptation is realized using the average values at both sides of the window. This technique is implemented via the following steps: (1) Locate the maximum or minimum point of the signal; (2) Determine gradients for a few steps at each point; (3) Allocate a window based upon the magnitude of the gradients; (4) Normalize the signal if needed. These steps are depicted in FIGS. 10a to 10d, respectively.

For the purposes of classification, it is useful to determine the type of defect as well as the situation where there is no defect. For these type of classifications the height, width, energy, area, geometric center, periodicity, peaks in the frequency, etc. of the windowed signal may be utilized for classification. Generally, any features from the time, frequency, spatial or other domains may be selected as part of the feature extraction process. The extracted feature information is stored as a feature vector defined as:

$$F(i)=[H_h(i)W_h(i)H_v(i)W_v(i)S_h(i)\ S_v(i)A_h(i)A_v(i) \ldots ]$$

where i is the image index; F(i) is the feature vector of the ith image; $H_h(i)$ is the height of the horizontal signal of the ith image; $W_h(i)$ is the width of the horizontal signal of the ith image; $H_v(i)$ is the height of the vertical signal of the ith image; $W_v(i)$ is the width of the vertical signal of the ith image; $S_h(i)$ is the bandwidth of the horizontal signal of the ith image; $S_v(i)$ is the bandwidth of the vertical signal of the ith image; $A_h(i)$ is the area of the horizontal signal of the ith image; $A_v(i)$ is the area of the vertical signal of the ith image; and so on. The selection of the appropriate features for feature extraction process is an off-line knowledge based process that is later described herein and depends on the application utilized.

Alternatively, a feature extraction module 60 may alternately utilize wavelet neural network comprising a number of neurons each comprising a fast wavelet transform to perform the feature extraction. The fast wavelet transform is defined as:

$$\psi_{a,b}(n) = \frac{1}{a}\psi\left(\frac{n-b}{a}\right)$$ Equation 25

Where a is the scaling factor and b is the translation. The choice for the value a is chosen to suit the particular application. It is presently preferred, for the purposes of feature extraction that scaling factors chosen are multiples of 2, e.g. a=$2^i$, i=0, 1, 2, 3 . . . etc. This greatly increases the computation speed of the system. It is further preferred that the original signals are compressed prior to the transform operation, instead of the dilating the wavelet.

In textile fabric environment the fast wavelet transform is defined as follows. The image of the fabric is represented by m(x, y) x, y∈Z. This image is scanned by bands of 128 pixels in width in both the horizontal and vertical directions. These bands are then averaged into 1-D signal streams s(n), n∈Z where n=x for horizontal bands and n=y for the vertical bands. The wavelet coefficients are represented by $Q_a(n)$. The values of a are 1,2,4,8 as described above where 1 represents the fast wavelet transform with the highest detail (highest frequency) and 8 represents the fast wavelet transform with the lowest detail (lowest frequency).

The wavelet transforms is implemented by convolving s(n) with the ψ(n) and φ(n) to obtain $Q_1(n)$ and $P_1(n)$ respectively. Where ψ(n) is the wavelet function and φ(n) is the scaling function. Then $Q_1(n)=s(n)*\psi(n)$ and $P_1(n)=\downarrow_2(s(n)*\phi(n))$ where * is the convolution operation and ↓2 represents decimation by 2 (sub-sampling). The functions ψ(n) and φ(n) are related by ψ(n)=φ(2n)−φ(2n−1). Subsequent scales of the wavelet coefficients ($Q_4(n)$, $Q_6(n)$ and $Q_8(n)$) are calculated as $Q_{2a}(n)=P_a(n)*\psi(n)$ and $P_{2a}(n)=\downarrow_2(P_a(n)*\phi(n))$. The presently preferred values for φ(n) are −0.129, 0.224, 0.836, and 0.483 and for ψ(n) are −0.483, 0.836, −0.224, −0.129.

It is also possible to both derive some of the feature values using the feature vector and obtaining some of the feature values utilizing the fast wavelet transforms to capture both time and frequency domain features of the 1-D signals.

3. Multi-Dimensional Wavelet Neural Network

Continuous Wavelet Transform formulas extend to the space $L^2$ (R) by using a separable product wavelet ψ(x)= $\psi_1(x)\psi_2(x)\ldots\psi_n(x_n)$ and squashing and translation vectors a and b, to construct:

$$\psi_{a,b}=\sqrt{|\text{diag}(a)|}\psi(\text{diag}(a)(x-b))$$ Equation 26

By linearly combining several such wavelets, a multiple-input/single-output neural network is obtained. The basic training algorithm is based on steepest descent. Rotation matrices are also incorporated for versatility at the expense of training complexity. A single-input/single-output multi-layer perceptron (MLP) can be cast as a truncated wavelet series. A linear combination of three sigmoid neurons is used to create each wavelet. The wavelet parameters are neither adapted, nor computed from prior Fourier Transform data analysis, but are taken incrementally from a predefined space-frequency grid of orthogonal wavelets. This approach prescribes learning as a multi-resolution, hierarchical procedure, and brings about the possibility of a type of network growth. The essence of multi-resolution learning is that a function can be approximated to arbitrary precision by starting with a coarse approximation at some resolution, and then successively adding layers of detail at higher resolutions. Higher resolution wavelet nodes are added to areas of the input space where the existing nodes contribute the largest errors.

Elliptic and radial wavelet neural networks (EWNNs and RWNNS) are extension of the intersection between Gaussian radial basis function (RBF) networks and wavelet networks. The local receptivity of RBF networks is adopted to obtain radially symmetric multidimensional wavelets of the form $$\psi_{a,b}=\sqrt{a^n}\psi(a\|x-b\|), a\geq 0$$ Equation 27

This results in a new class of RBF neural networks referred to as radial WNNs. Whereas RBF networks represent functions in terms of time atoms, the WNN employs time-frequency atoms. To illustrate, a basic scalar wavelet that will be recurrently employed is defined as:

$$\cos trap(x) = \cos\left(\frac{3\pi}{2}x\right)\min\left\{\left\{\max\frac{3}{2}(1-|x|), 0\right\}, 1\right\}$$ Equation 28

Figure 11:
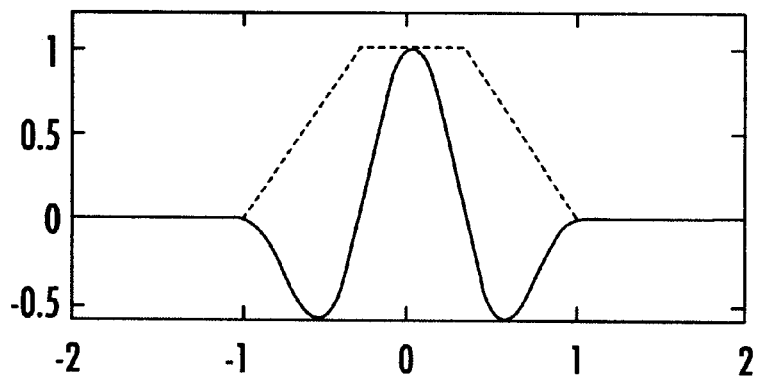
FIG. 11 is a graphical representation of a basic Costrap Wavelet utilized in conjunction with the presently preferred wavelet neural network according to the present invention.
Figure 12:
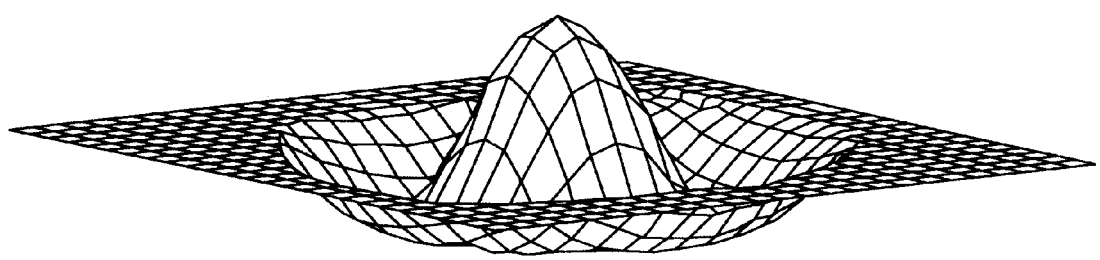
FIG. 12 is a graphical representation of a basic Bivariate Costrap Wavelet utilized in conjunction with the presently preferred wavelet neural network according to the present invention.

This function, shown in FIG. 11, consists of two cycles of the cosine function, windowed by a trapezoid that linearly tapers two thirds of the endpoints to zero. Many other wavelets are possible, but highly oscillatory basis functions result in an undesirable lack of smoothness in the learned model. Taking ψ(x)=cos trap(x) and substituting a=1, b=0 in Eq. 26, induces the two-dimensional basic wavelet shown in FIG. 12. A two-dimensional RWNN implements a linear combination of a family of these surfaces, deployed throughout the plane with various centers, widths and heights.

The feature of adaptive anisotropy an be accommodated by computing a more general distance between row-vectors x and b, with wavelets in the form $$\psi_{A,b}(x)=|A|^{1/4}\psi(\sqrt{(x-b)A(x-b)^T}), A\geq 0$$ Equation 29

These types of wavelets constitute the basis for a new class of elliptic basis function networks termed elliptic WNNs. A symmetric positive semi-definite squashing matrix A, with equal scales $1/a^2$ along all coordinates, A=diag ($a^2$, . . . , $a^2$).

For function estimation problems, the complete WNN is defined by $$\hat{y}=[\psi_{A1,b1}(x), \psi_{A2,b2}(x), \ldots \psi_{AM,bM}(x)]C+[x1]C_{lin}$$ Equation 30 where
x=1 x n input row-vector
ŷ=1 x m output row-vector
Aj=n x n squashing matrix for the $j^{th}$ node
bj=1 x n translation vector for the $j^{th}$ node
C=m x m matrix of output coefficients
$C_{lin}$=(n+1) x m matrix of output coefficients for the linear portion
n=number of inputs
M=number of wavelet nodes
m=number of outputs.

The $\psi_{Aj,Bj}$ in Eq. 30 are those defined in Eq. 29, but without the reenergization factors, which are absorbed by C. The energy factors are still needed for wavelet analysis. The complete WNN structure includes a linear portion shown in FIG. 13. For classification problems, the output vector y is cascaded with a competitive layer. The outputs enter a competition, and the maximum becomes 1 while all others 0. The I occurs at a position that determines the input's class. For dichotomies, there is a choice between two competitive outputs, or a single output y cascaded with a unit step or a bipolar function. Therefore, the output of the WNN provides for the potential indication of the existence of the predetermined patterns or defects from the known set, while the competition function determines which of the known patterns or defects has been detected.

i. WNN Data Preprocessing

In implementing a multi-dimensional WNN, the nature of one input variable may be quite different from that of any other input variable into the network. In such cases, it is expedient to standardize the inputs by computing the z-score $$z_1 = \frac{x_1 - \bar{x}_1}{\sigma_1} \quad \text{Equation 31}$$

where $$\bar{x}_1 = \frac{1}{N} \sum_{i=1}^{N} x_1^i, \quad \delta_{xi} = \sqrt{\frac{1}{N-1} \sum_{i=1}^{N} (x_1^i - \bar{x}_i)} \quad \text{Equation 32}$$

are the sample mean and standard deviation respectively, and x and the ith component of the input datum available in the training set T. Once x, and $\sigma_x$, are computed for all dimensions i=1, . . . , n, a mean vector x and standard deviation vector $\sigma_x$ are stored and made part of the whole WNN scheme. That is, whenever a network output is requested, the inputs are first normalized using these fixed parameters. While theoretically, the omission of this step does not affect the approximation capabilities of the WNN, in practice it is an effective way of systematizing and controlling for the round-off errors of disparate magnitudes. The rationale for the inclusion of the linear portion in the complete WNN is that the non-linearities introduced by the WNN are preferably utilized only to the extent that they can help improve the approximation of a function. If there exists a linear trend in the input-output structure of the data, it can be quickly accounted for by using a hyperplane. Instead of having several nodes working to construct such plane, the wavelet nodes are allowed to concentrate all their efforts on the "wave-like" components of the hypersurface. Let P be an Nxm matrix of targets obtained by stacking the N input row-vectors (usually standardized) in the training set. Let T be the Nxm matrix of targets by stacking the corresponding output row-vectors. Then the linear portion of the WNN is trained in one step via:

$$C_{lin} = \left\{ \begin{bmatrix} P^T \\ 1_{1 \times N} \end{bmatrix} [P \ 1_{N \times 1}] \right\}^{-1} \begin{bmatrix} P^T \\ 1_{1 \times N} \end{bmatrix} T \quad \text{Equation 33}$$

where 1 has N "ones." In rank-deficient cases, the slower but more robust pseudoinverse should be used.

The nonlinear portion must then account for the remaining, "unexplained" component in the input-output mapping. This residual is a detrended version Td of the targets. The training of the wavelet nodes then proceeds with P and Td as training inputs and outputs, respectively. It should be noted that the detrending step is preferably done only once prior to training. In actual use, there is no "retrending" to do on the WNN output since the trended component of the output is accounted for by $C_{lin}$. As with standardization of the input variables, this step should not preferably add to the approximation capabilities of the purely nonlinear WNN, but does result in significantly more efficient solutions.

ii. WNN Structure Identification

Universal approximation theorems predict that with "sufficiently many" computing elements, functions can be approximated arbitrarily well using the known neural networks. These theorems give minimum information as to how many elements are necessary, where elements should be placed in the space of parameters, or how they should be connected. Common neural network practices have been widely criticized for this lack of design criteria, calling for an extensive amount of trial and error.

Figure 13:
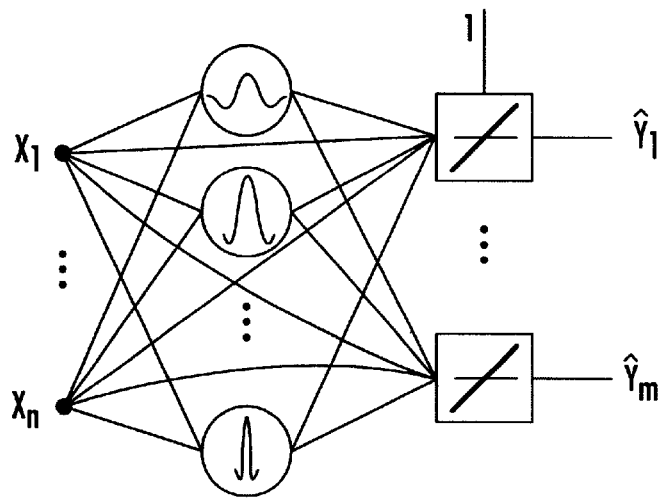
FIG. 13 is a diagram of a presently preferred topology of a multi-dimensional wavelet neural network according to the present invention.

The structure identification of a model has two fundamental parts. One part refers to the choice of inputs believed to correlate to the output in question. The second part refers to size or order of the model. The structure of the WNN consists of number of inputs, number of outputs, number of wavelet nodes, and connection topology. The number of outputs is determined by the problem definition, i.e., the number of predetermined defects or patterns that are to be classified. The internal topology is defined such that full connectivity is always available, as shown in FIG. 13. What remains to be determined is the number of wavelet nodes in the WNN. Each data cluster in the input-output product space where data reside tells us that there exists a relationship between neighboring inputs in certain region of the input space, and neighboring outputs in certain region of the output space, that can be systematically found based on K-means clusterings of the training data in this space for a successively larger number of clusters. Each clustering is assigned a measure of within-to between-variance of the clusters. The measure is the inverse of an F-ratio generalized to multiple dimensions, $$\frac{1}{F} = \frac{\sum_{j=1}^{K} \sum_{i=1}^{N_j} \|w_j^i - \bar{w}_j\|^2 / (N - K)}{\sum_{j=1}^{K} \|w_j^i - \bar{w}_j\|^2 / (K - 1)} \quad \text{Equation 34}$$

where K is the number of clusters, w=[x y] is an augmented input-output vector, $w_j^i$ is a datum vector that belongs to the $j^{th}$ cluster, Nj is the number of such points in the jth cluster, w is the center of the jth cluster, and W is the grand mean. K is increased from two clusters to any tolerated limit. The smaller 1/F is the better the clustering. The number of wavelet nodes is taken to be the minimizer of this measure. It should be noted that Kmeans is a greedy algorithm that finds a locally optimal solution to this series of NP complete problems. There is no guarantee that the number chosen via the use of Eq. 30 will result in the most theoretically optimal WNN structure. Nevertheless, the result produced discriminates adequately when the input consists of noisy data, as it has a tendency to yield economical (therefore less prone to becoming overfit) WNNs.

iii. WNN Parameter Identification

Once a model structure has been chosen, a set of parameters within that structure must be found. In this section, the initialization of the WNN parameters, and two training algorithms: Levenberg-Marquardt for average squared error, and a genetic algorithm of ranking type for any kind of error measure are utilized. The linear portion parameters $C_{lin}$ of the complete WNN are left fixed. Therefore, in the following discussion, parameter identification refers to the determination of the nonlinear portion of the WNN: $A_j$, $b_j$, and C.

iii.a Initialization from Structure Identification

A by-product of the structure identification procedure in the previous section is that reasonably good initial parameters are either already available, or easily obtained from first and second order statistics. For the input-output clustering methods, the initial wavelet centers $b_j^0$ are derived by projecting the cluster centers onto the input space. The squashing matrices are set to where is the covariance matrix of the input data within the jth cluster. Finally, the linear coefficients $C_0$ are obtained exactly as for the coefficients $C_{lin}$ but using post-transformed patterns and detrended outputs.

iii.b Levenberg-Marquardt Algorithm

The Levenberg-Marquardt (LM) Algorithm is a compromise between the steepest descent and the Newton method. For a multivariate function, g, the Levenberg-Marquardt update law is $$\Delta\theta = \bar{H}^{-1} \nabla g(\theta_k) \quad \text{Equation 35}$$

where $\theta$ is a $N_p \times 1$ vector of parameters $$\nabla_g(\theta_k) = \left[ \frac{\partial g}{\partial \theta_i} \cdots \frac{\partial g}{\partial \theta_i} \right]^T$$

is the gradient of g—evaluated at $\theta_k$, H is the Hessian matrix with entries $$(H)_{ii} = \frac{\partial^2 g}{\partial \theta_i \partial \theta_i}$$

evaluated at $\theta_k$ and H has the same entries as $\bar{H}$ except that the diagonal has $(H)_{ii} = (1+\lambda)(H)_{ii}$.

Especially in the early phase of the procedure, when the initial approximations may be far away from the solution, the parabolic will lead to results that keep increasing in inaccuracy. Thus, whenever it is found that the next guess $\theta_{k+1}$ would increase, rather than decrease g, dimensional $\lambda$ is increased by some factor (e.g., 10) and a more steepest-descent-like step is attempted until improvement is seen. Similarly, when the next guess seems to work correctly, $\lambda$ is decreased, thus accelerating the convergence via Newton-like steps.

In many practical situations, it is adequate to cast the objective functional g in the form of a least squares problem. For a fixed network structure, the training of the WNN requires a minimization of the arithmetic average squared error $$ASE(\theta) = \frac{1}{N} \sum_{i=1}^{N} \left( y^i - \hat{f}(x^i, \theta) \right)^2 \quad \text{Equation 36}$$

This measure is an appropriate error criterion in conjunction with the LM algorithm by virtue of possible differentiability. The kth element of the gradient is $$\frac{\partial ASE}{\partial \theta_k} = -2\frac{1}{N} \sum_{i=1}^{N} \left( y^i - \hat{f}(x^i, \theta) \right) \frac{\partial \hat{f}(x^i, \theta)}{\partial \theta_k} \quad \text{Equation 37}$$

The Hessian has elements $$\frac{\partial^2 ASE}{\partial \theta_k \partial \theta_l} \approx 2\frac{1}{N} \sum_{i=1}^{N} \frac{\partial \hat{f}(x^i, \theta)}{\partial \theta_k} \frac{\partial \hat{f}(x^i, \theta)}{\partial \theta_l} \quad \text{Equation 38}$$

Thus, only the gradient needs to be supplied, which depends on the basic wavelet chosen for the WNN. For this training method, the vector $\theta$ is a concentration of all the WNN parameters (except $C_{lin}$ and preprocessing quantities). For the EWNNS, we require the squashing matrices to be symmetric, so only the upper triangle of each matrix needs to appear in $\theta$ (there are $n(n+1)/2$ parameters per wavelet node).

iii.c Genetic Algorithm

The basic idea behind genetic algorithms (GAs) is that candidate solutions can engender "children" solutions whose average performance is better than their "parent" solution. Because only the fittest candidates survive at each generation, the parents must have been already good at solving the problem under consideration. The children inherit the good attributes of their parents, but by also introducing novelty, they become either better or worse. The worst ones perish, so the remaining population can only be better. The same principle carries over to future generations, and evolution results. To apply this idea by computer means, a code is first established that maps any trial solution onto a string of genes (binary digits) called a chromosome. Each parameter can be encoded as a $N_b$-bit string, and a large chromosome representing the whole system can be created by concatenation. Alternatively and presently preferred, the system can be encoded as Np separate chromosomes-one for each parameter dimension.

Following this approach, Np populations with Npp individuals are initially chosen. Then the following four steps, which define one generation, are iterated until some stopping criterion is met:

1. Evaluation. Each individual in the current population is evaluated with respect to the cost functional, and ranked according to performance.
2. Reproduction. The 20% fittest candidates produce two copies of themselves, which are passed to the next generation. The next 60% pass a single copy of themselves to the next generation. Individuals in the bottom 20% do not reproduce, perishing at the current generation. This scheme preserves the number of individuals in every population.
3. Recombination. Two individuals are randomly chosen from the population, and their genetic material is crossed over. The crossover point is randomly placed anywhere between the first two and the last two genes. This procedure is repeated until a fraction $P_{rec}$ of the whole population has been recombined.
4. Mutation. Every gene of every individual has a probability $P_{mut}$ of being toggled. This step prevents suboptimal individuals (local minimizers of the cost functional) from becoming winners all the time, giving a chance to new, "strange" individuals.

The initialization procedures yield a squashing matrix $A_j^o$ for each node. Each of the upper triangle entries of $A_j^o$ is searched over an interval $[0.1^o jkl, 10a^o jkl]$ where $a^o jkl$ is the (k,1)th entry of $A_j^o$. The complete search space consists of these intervals, in Cartesian product with the smallest hyper-rectangle containing T. The latter defines the search space for the translation vectors $b_j$. The output WNN coefficients are obtained for each candidate via regression at each generation.

iii.d Simultaneous Structure and Parameter Identification

When computational expense is not the primary concern, the correct size of the network is determined following the principle of parsimony, i.e., the "correct" network is preferably the smallest WNN that meets performance requirements. Such network may be found by applying a simplest-to-sufficient strategy, where the network size is systematically increased and a candidate solution is determined at every step. That is, structure and parameter identification are intertwined in an evolutionary loop. When applied to the method of input-output clusterings, the number of wavelet nodes is varied from M=2 until sufficiency, and an initial WNN is obtained for each M via a first and second order statistics of the clusters projected to the input space.

It should be noted that the outputs of the WNN determine whether and to what degree the input signal may belong to a particular defect class.

Figure 14:
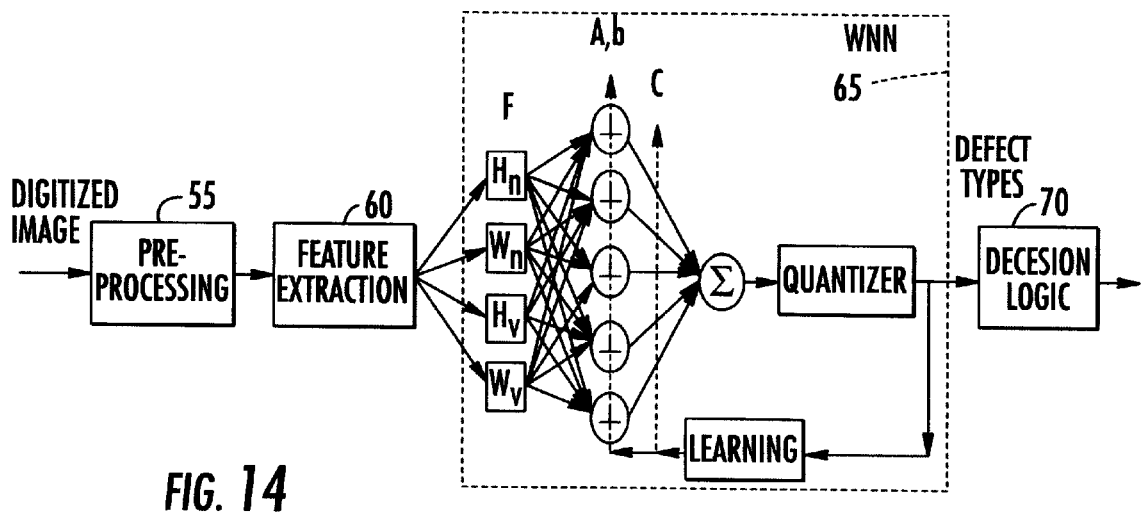
FIG. 14 is a diagram depicting the presently preferred functionality of a multi-dimensional neural network utilized in the pattern recognition system of the present invention.
Figure 15:
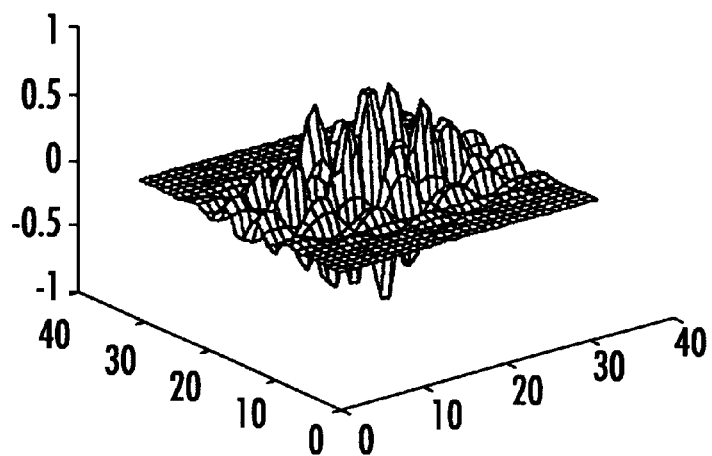
FIG. 15 depicts a presently preferred Morlett wavelet that is utilized by the WNN of the present invention.

Referring to FIG. 14, the WNN 65 is developed and trained as described above. The WNN provides a multidimensional nonlinear mapping that relates the feature vector to the identification result. Then, it is straightforward to obtain identification results from input features. The example WNN 65 of FIG. 14 utilizes multiple inputs and outputs but only a single layer. The individual wavelets can be described as according the following equation:

$$\psi_{A,b}(x) = |A|^{1/4}\psi((x-b)A(x-b)^T)^{1/2} \qquad \text{Equation 39}$$

where x is the input row vector, i.e., F(I) in this application; A is the squashing matrix for the wavelet; b is the translation vector for the wavelet; T the transpose operator; $\psi$ the wavelet function, which is preferably the costrap wavelet as described in Eq. 28 or a Morlett wavelet shown in FIG. 15. The term $(x-b)A(x-b)^T$ in the description actually implies some distance concept between the input and the wavelet location, which is defined as an elliptical and denoted as $\|x-b\|_A$. If the input represents some features, then this term accounts for how far the feature subspace weaved by the wavelets are located from the expected feature subspace.

The WNN is formulated as:

$$y=[\psi_{A1,b1}(x)\psi_{A2,b2}(x) \ldots \psi_{AM,bM}(x)]C[x1]C_{lin} \qquad \text{Equation 40}$$

where n is the number of inputs, M the number of wavelet nodes, m the number of outputs, x the 1×n input row-vector, y the 1×m output row-vector, $A_j$ the n×n squashing matrix for the jth node, $b_j$ the 1×n translation vector for the jth node, C the M×m matrix of output coefficients, $C_{lin}$ the (n+1)×n matrix of output coefficients for the linear portion. For a single output, Equation 34 can also be expressed in a summation format as:

$$y=[\psi_{A1,b1}(x), \psi_{A2,b2}(x) \ldots \psi_{AM,bM}(x)]C+[x1]C_{lin} \qquad \text{Equation 41}$$

where we omit the linear portion and write $A_1, A_2, \ldots A_M$ into the matrix A.

Further, the output of the WNN is designed as:

$$y = \sum_{j=1}^{M} c_j \psi\left(\sqrt{(x-b_j)^T A(x-b_j)}\right) \qquad \text{Equation 42}$$

which acts as a classifier or identifier utilizing a competition function which is preferably defined as:

$$z_i = \{1 \text{ if } y_i \geq y_j \text{ and } y_i \text{ is encountered before } y_j (j=1, \ldots, m \text{ but } \neq 1) \qquad \text{Equation 43}$$

The criterion for training the WNN is chosen as:

$$AME = N_w/N \qquad \text{Equation 44}$$

which stands for the average classification error where $N_w$ is the number of wrong classifications and N is the number of total classification trials. For example, we got AME=40% if we misclassified 4 images out of 10 images using the WNN. Genetic Algorithms (GA) are employed to train the WNN since the relation between the input (features) and the output (defect types) is severely nonlinear. The fitness function is designed as I-AME. If there is no classification error, i.e., AME=O, then the fitness value is the maximum.

The output of the WNN, i.e., z, is further coded into a binary string (C1C2C3C4) for the purpose of easing the optimization tasks where $c_i$ (I=1,2,3,4) denotes a binary bit. For example, (1000) indicates a horizontal defect, (0100) a vertical defect, (0010) an area defect and (0001) no defect. This binary representation may equalize the distances between any two output points in the output space such that they have same chances to be optimized. Besides, it needs some effort to find an appropriate network structure and network parameters. Structure and parameter identification procedures for the construction of the WNN as described previously are exploited in a fabric defect identification work.

Figure 16:
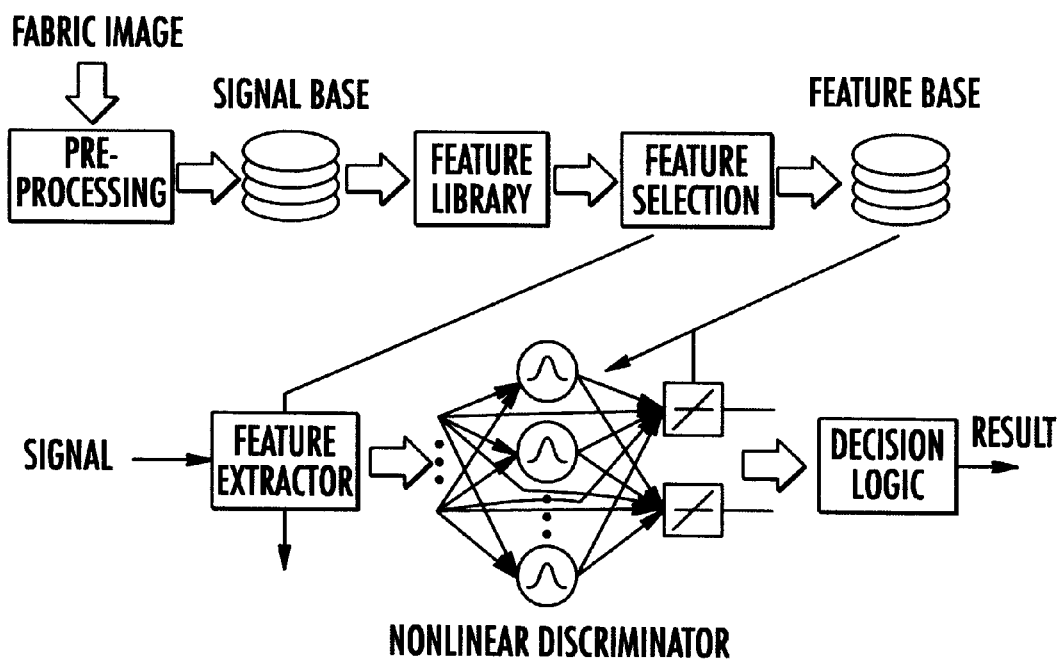
FIG. 16 is a diagram of the presently preferred distribution of the identification and classification functionality according to the present invention.

Referring to FIG. 16, the off-line portion 200 is the training portion of the system that provides the information for determining which features of the signal are measured by the feature extractor 60 and the weights of the wavelets in the WNN 65. The problem of feature extraction is determining what aspects of the input signal should be isolated for application to the classifier, i.e. what features to select. The vision systems employed in industrial pattern detection process, e.g. fabric inspection, typically generate massive amounts of multidimensional data that is corrupted by noise and exists in a cluttered environment. It is important to be able to data-mine, fuse, filter and or otherwise extract useful information from the raw data. This can be accomplished by decreasing the complexity of the input space or increasing the computational capability of the processor, or both. To reduce the cost and complexity of a pattern detection system it is preferred to view the problem of feature extraction as it relates to the fundamental intelligent task of inductive classification. It should be noted that criteria for feature selection are dependent on the application for which the pattern recognition system is being utilized. This is because the characteristics of the materials and faults will determine which set or class of features has the greatest differentiation between the fault and normal states.

For a given set of a decision that follows Bayes' rule with respect to a predefined feature set, it is also known how to create near optimal classifiers empirically using artificial neural networks. However, the given feature set may not convey maximum information from data available to the system, e.g. best exemplify the faults or patterns from the available multidimensional input data set. The act of prescribing the features themselves is routinely dismissed as an "art"—an inductive problem guided only by trial-and-error and experience. The basic premise is that since a quantitative feature is a formula or algorithm that maps a raw data input set into a scalar, artificial neural networks can learn not only how to implement a given map, but also how to create maps that result in sensitive features following a pseudo-inductive approach. In contrast to predefined feature selection, this is a problem of creating optimal artificial features, i.e. manipulating the input data in such a way as to generate signals that when faults occur accentuate the portion of the signal that represents the fault. The problem is equivalent to extracting maximum relevant information from raw data for a given discrimination task.

The process of feature selection builds a feature library which is built from the signal base that is made up of training signals that represent the particular defects that are known to exist in the products produced by the process. The determination of the features to select from the signal base can be determined by simple statistical analysis that correlates the features of the signal to each other. The selected features and magnitudes are also provided to a feature base which is utilized to map the experimental input-output data. In the present invention this is done by utilizing multi-input multi-output WNNs.

4. Decision Logic Module

The decision logic module 70 fuses or integrates information from the preprocessing module 55, the feature selection module 60 and the WNN module 65. The decision logic module 70 performs the functions of resolving conflicts of the WNN module 65, when the WNN module 65 identifies the detected pattern as potentially being more than one of the predetermined pattern. The decision logic module 70 can also be utilized to provide a final declaration to the existence of a defect, if the pattern recognition system 50 is utilized as part of a FDI system, and can also determine the degree of certainty of the classification of the detected pattern as the predetermined pattern.

Decision logic module 70 is preferably provided with the scanned image, e.g. the fractal, horizontal or vertical scan depending on the application, the feature values determined during feature extraction, and the outputs of selected neurons of the WNN module 65. The decision logic module 70 then determines by interpolation which of the potential predetermined patterns the detected pattern is closest, in terms of the input to the pattern detection system 50. This can be done by simply comparing the values obtained in the training for each of the fractal, horizontal or vertical scan depending on the application, the feature values determined during feature extraction, and the outputs of selected neurons of the WNN module 65 to the values for the detected pattern and averaging the result to see which values are the closest.

B. FDI System

Figure 17:
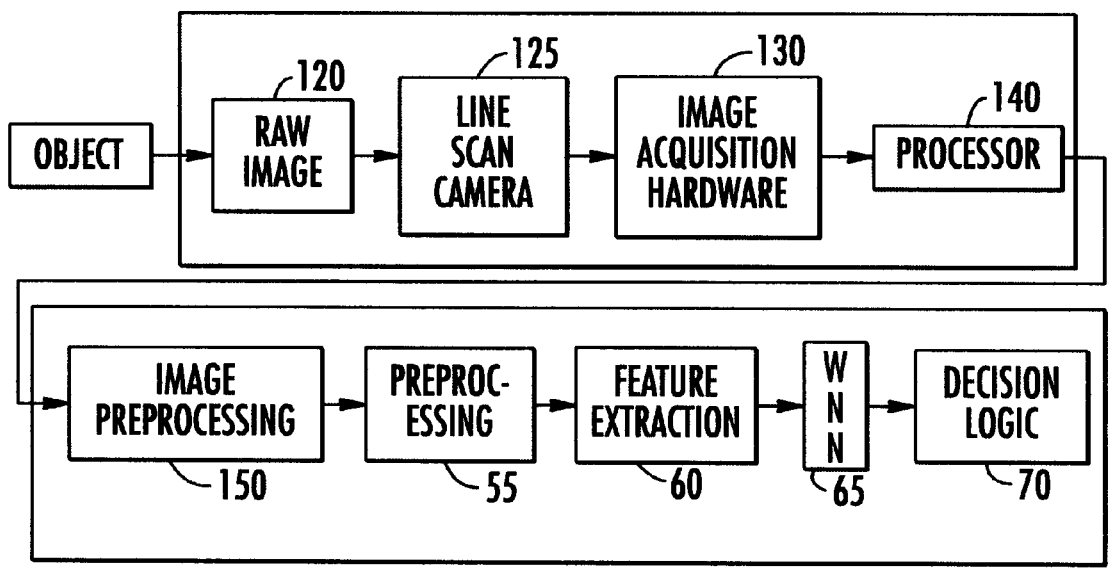
FIG. 17 is a block diagram of the presently preferred FDI system incorporating the presently preferred pattern detection system according to the present invention.

Referring to FIG. 17, the FDI system incorporating the pattern identification system is composed of two major parts: a software portion 105 and a hardware portion 100. The system operates using a two step approach including off-line operation that trains the identification mechanism and on-line operation that uses the trained mechanism to fulfill real-time identification tasks.

Object 110 can be any physical object about which an image can be extracted. Although the presently preferred FDI system is utilized for fabric, other objects that are generally two-dimensional can be utilized in accordance with the present invention such as metal, paper, food, glass, lumber, etc. Raw images 120 represent images within the region of interest of the object 110. The raw images can be of the whole object or areas of the object where the potential patterns may exist. The raw images 120 may be obtained by a Line Scan Camera which is a high-speed camera used to acquire analog or digitized images. Image acquisition hardware 130 is utilized prepare the image in such a way as to make useable by the computer system. The image acquisition hardware 130 may include the functions of a frame grabber or other image acquisition hardware such as A/D and associated processing devices used to transfer and retain images. Processor 140 is designed to process raw data and declare defects and is associated with an on-board memory that stores imaging data and algorithms used by the processor 140. The processor 140 may be a pentium processor but however is preferably a DSP processor to increase the processing speed of the pattern detection system.

The software system 105 includes image preprocessing module 150 that processes raw images in order to maximize the contrast between the target image (defect) and the background. Typical preprocessing techniques which can be utilized with the present invention include edge detection/enhancement, de-noising, segmentation, compression, filtering, 2-D wavelet transformation, or other similar process. Image preprocessing block does not need to be included as part of software system 105. However, image preprocessing module 150 may be useful in situations where the image generated is high noise, either in its entirety or in various sections, is weak, or large in size. Preprocessing module 55 projects 2-D images into 1-D waveforms or signals. This is generally done in order to simplify and increase the processing speed of the detection and identification algorithms in real time applications. Preprocessing module 55 also processes the signals to improve the signal to noise ratio of the scanned signal in order to allow for more accurate defect detection. Some techniques that may be utilized as part preprocessing module 55 include high-pass filtering, low-pass filtering, median filters, maximum scanning, windowing, or other similar process. Feature extraction module 60 extracts predetermined features from the processed signals so as to prepare identification. Generally, the process of features extraction entails two-steps, feature selection and feature extraction. Feature selection is an off-line intelligent process while feature extraction is an on-line algorithmic process that takes place in real time to prepare the signals for pattern identification. Possible features that may be extracted from the real time 1-D signals provided after operation by signal preprocessing module could include peak, width, slope, area, multipeaks, spectrum, cepstrum, or the like. The key to feature extraction is the off-line knowledge based selection of the features likely to be indicative of the existence of the predetermined patterns or defects. Wavelet neural network (WNN) module 190 can act as the pattern identifier alone or the pattern identifier and classifier depending on the desired application. The detection or non-detection of the pattern can be utilized by results module 200 that can provide the final results including probably graph, text, sound, video, etc. The results module is not necessary for the systems, and the output of the WNN module 65 can be provided directly to a control system or other equipment if no human user output is required. Specifically, based upon the result of the classification of the defect the user of the device can program the device to alter certain parameters based upon the type of defect class.

C. Fractal Scanning

The FDI system of the present invention preferably involves analysis of 1-D data. However, it can be applied to 2-D images by using specialized scanning techniques at the preprocessing stage. Analysis of images for the purpose of FDI requires information in both the horizontal and vertical directions to acquire maximum information about the features in the image. However, analysis in 2-D is computationally intensive and time consuming. Hence, a better approach is to scan the image into a 1-D stream of data. Unfortunately, commonly used scanning techniques which scan the image into a 1-D data stream, such as raster scanning, do not preserve the adjacency of the features in the direction perpendicular to the direction of scanning. Feature extraction for FDI is easier in 1-D scanning techniques that retain the neighborhood relationship of the image. Thus, a technique that scans one area of the image completely before moving to the next area is desirable. In accordance with the present invention, a fractal scanning technique is used which is much more efficient at capturing features in digital images than other scanning techniques. The specific scanning method selected will depend on the application, the alignment of the defects on an image. This process is preferably performed in the preprocessing module 55.

Fractal scanning is very suitable for the purpose of FDI because of the inherent scaling and nesting properties of fractals. The following attributes of fractal scanning make it ideal for this application: (1) fractal scanning is nested recursively in a self similarity manner; (2) it moves in all directions of interest within the lowest dimension of the image; (3) it preserves the adjacency of the image features in all directions; (4) it is scaleable to the required resolution due to the fractional dimension; (5) it allows for a substantial reduction in data; (6) it assists in reducing the amount of calculations; and (7) it enables the availability of 1-D instead of 2-D data.

Unfortunately, thus far none of the studies involving fractal scanning have given a systematic and organized algorithm for generating the fractal scan. In accordance with the present invention, a detailed mathematical representation of a fractal scanning technique has been developed and is presented here which provides a very reliable and efficient scanning technique for fault detection.

Figure 18:
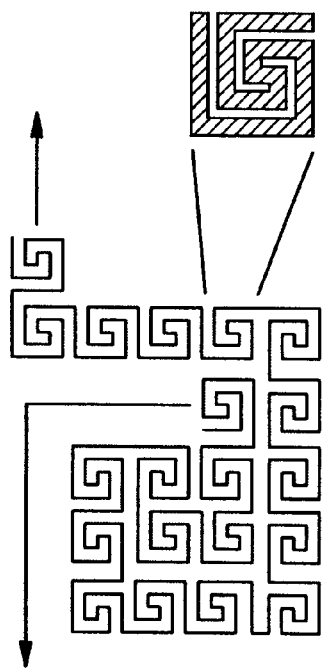
FIG. 18 depicts the nested hierarchy of a two-level fractal.
Figure 19:
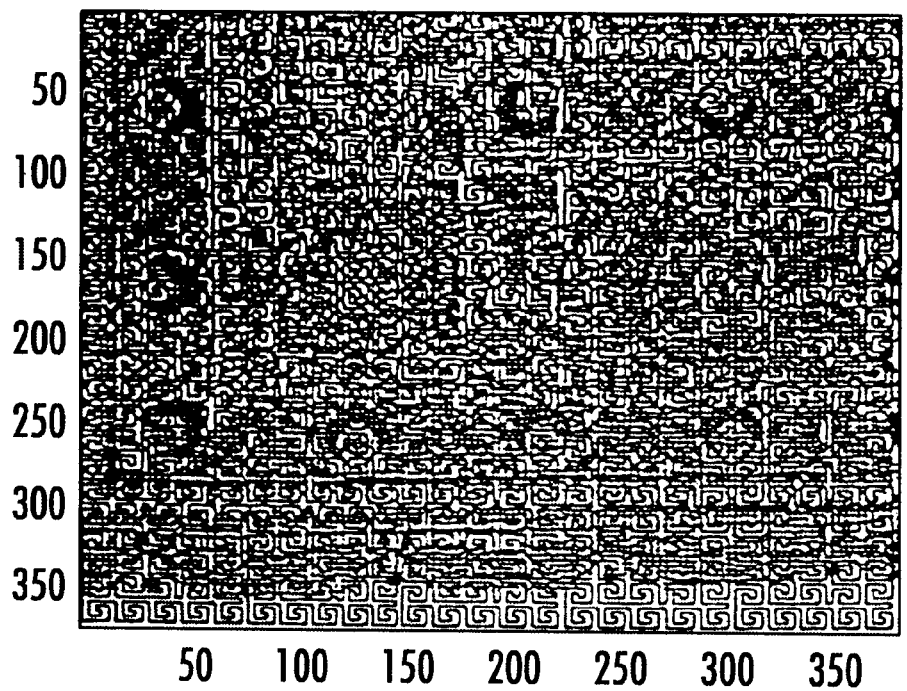
FIG. 19 illustrates a complete fractal scan over an image of a carpet.

The ability of the fractal scan to capture the faults of smallest dimension comes from the self similarity nesting property of the fractals. Each fractal is composed of self similar fractals of smaller size and so on. The recursion continues until the size of the fractal is comparable to the size of the smallest anticipated fault. The nested hierarchy of a two level fractal is shown in FIG. 18. The final fractal is one continuous line whose length depends upon the dimension of the fractal. An example of the complete fractal scan over the image of a carpet is shown in FIG. 19.

Figure 20:
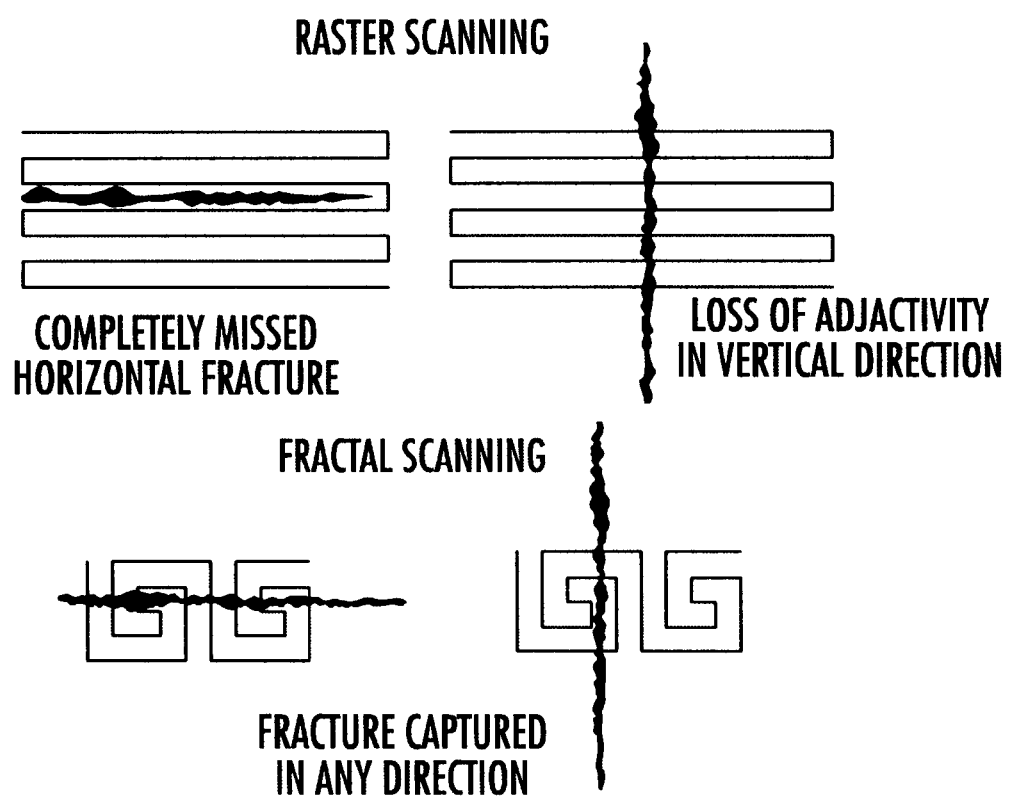
FIG. 20 illustrates the advantages of fractal scanning over raster scanning for FDI.

As mentioned above, the fractal scanning technique preserves the neighborhood relationship in an image. The intricate geometry of a fractal provides the liberty to scan less than the total number of pixels without loss in detectability of the methodology. This introduces the scale factor s which represents the number of pixels omitted between two lines. The problem with conventional scanning, such as raster scanning, is that it can completely miss a fault feature in the horizontal direction if the dimension of the fault in the vertical direction is less than s. On the other hand, if a fault occurs in the vertical direction, the vertical adjacency of the feature is lost as the scan goes all the way to the end of the image and comes back to read the feature again. Hence, a very critical sequence of pixel intensities can be lost as these pixels occur too far apart in the data stream. Both of these scenarios are shown in FIG. 20. It can be seen from FIG. 20 that the likelihood of missing a fault is low when using the fractal scanning technique. Moreover, the proximity relationship is better retained as compared to the conventional scanning techniques. The fractal scan crosses the fault at a number of places which are in close proximity to each other.

FIG. 21a illustrates the preferred basic fractal used for this algorithm. It will be apparent to those skilled in the art that fractals different from the one shown here can also be used depending upon the nature of the application. This shape of the fractal is particularly suited for textile fabric inspection due to the orthogonal nature of the faults in textile fabrics, to which the pattern recognition scheme is applied in accordance with the preferred embodiment.

To provide an example of a mathematical representation of the fractal, a basic fractal is resolved over a 5×5 grid as shown in FIG. 21b. Each box on the grid is itself a similar fractal repeating itself with a different orientation, θ, given by the direction of the arrow. It is seen that the fractal in FIG. 21a starts from the top left corner and ends at the top right corner. The net displacement can be represented by the direction vector (1,0). Hence the orientation of this fractal is at an angle of 0 radians. It can be seen that the orientation of the sub-fractals in FIG. 5b is one of the following angles:

$$0, \frac{\pi}{2}, \frac{2\pi}{2}, \frac{3\pi}{2}$$

or $$\theta_n = \frac{n\pi}{2} \quad n = 0, 1, 2, 3$$

The representation n=4, 5, . . . are mapped back to the principal argument (n=0, 1, 2, 3). Therefore the definition of only these four orientations is necessary to accomplish the connectivity of the whole fractal.

Let a fractal be represented by $f^r_n$, where r=0, 1, 2 . . . , L, is the level of the fractal in the nested hierarchy. L is the total number of levels. A larger value of r represents a fractal of larger physical dimension. $n \in \{0, 1, 2, 3\}$ represents the orientation of the fractal given by the angle nπ/2. The nested arrangement for a fractal with orientation n and level r is given by an ordered set as shown below:

$$f^r_n = (f^{r-1}_{n_1}, f^{r-1}_{n_2}, f^{r-1}_{n_3}, \ldots , f^{r-1}_{n_k}) \quad \text{Equation 45}$$

where $n_1 \ldots , n_k$ are the orientation for sub-fractals in the sequence they are connected and K is the number of sub-fractals in one fractal (25 in this case).

The orientation of the sub-fractals for the basic fractal are obtained from FIG. 5b. Starting from the top left corner, the first box has an orientation of $$\frac{3\pi}{2}$$

or n=3. Hence the first subfractal of the basic fractal $f^L_0$ is $f^{L-1}_3$. Moving along in the direction of the arrow, the next box is also pointing down which refers to $f^{L-1}_3$. Continuing the same argument, the third and the fourth subfractals have the same direction and the fifth one has direction 0. This implies a sub-fractal $f^{L-1}_0$. Likewise, completing the directions of all the 25 sub-fractals, the representation of the basic fractal becomes:

$$f^L_0 = (f^{L-1}_3, f^{L-1}_3, f^{L-1}_3, f^{L-1}_3, \qquad \text{Equation 46}$$
$$f^{L-1}_0, f^{L-1}_0, f^{L-1}_0, f^{L-1}_0, f^{L-1}_1,$$
$$f^{L-1}_1, f^{L-1}_1, f^{L-1}_1, f^{L-1}_2, f^{L-1}_2,$$
$$f^{L-1}_2, f^{L-1}_0, f^{L-1}_3, f^{L-1}_3, f^{L-1}_1,$$
$$f^{L-1}_1, f^{L-1}_1, f^{L-1}_1, f^{L-1}_0, f^{L-1}_0, f^{L-1}_0)$$

For simplicity, the fractals are associated with direction set θ. For the basic fractal, the direction set is given as:

$$\theta_0=(3,3,3,3,0,0,0,0,0,1,1,2,2,2,0,3,3,2,1,1,1,1,0,0,0) \quad \text{Equation 47.}$$

The elements of the direction set $\theta_n$ are represented by $\xi^n_i \in \{0,1,2,3\}$, and are related to the direction $\theta_{\xi_i}$ of a sub-fractal by:

$$\xi_i = \frac{\theta_{\xi_i}}{\pi/2} \quad i = 1, \ldots, 25 \qquad \text{Equation 48}$$

Once the representation of the basic fractal is complete, fractals with other orientations can be generated. As stated above, only four orientations, given by $$\theta = 0, \frac{\pi}{2}, \frac{2\pi}{2}, \text{ and } \frac{3\pi}{2},$$

are required. All these orientations can be derived from the basic fractal. In general, a mapping from any orientation to another one can be calculated. For (m,n)=(0,1), (1,0), (2,3), (3,2), $f_o \leftrightarrows f_1$, $f_2 \leftrightarrows f_3$ are reflections across the line y=x in the xy-plane. If $$\theta_n = \frac{n\pi}{2}$$

is the angle at which a fractal is oriented, represented by $(\cos\theta_n, \sin\theta_n)$, then mapping $f^r_{n \to f^r_m}$ is given by:

$$(\cos\theta_m \quad \sin\theta_m) = (\cos\theta_n \quad \sin\theta_n)\begin{pmatrix} 0 & 1 \\ 1 & 0 \end{pmatrix} \qquad \text{Equation 49}$$

$$\theta_m = \tan^{-1}\left(\frac{\cos\theta_n}{\sin\theta_n}\right)$$

$$\theta_m = \theta_n + \frac{\pi}{2}(-1)^n, (m, n) = (0, 1)(1, 0)(2, 3)(3, 2)$$

Similarly the transformation for (m,n)=(1,2), (2,1), (3,0), (0,4), respectively, is the reflection across the line y=−x. The transformation matrix is $$\begin{pmatrix} 0 & -1 \\ -1 & 0 \end{pmatrix}$$

which gives $$\theta_m = \theta_n - \frac{\pi}{2}(-1)^n, (m, n) = (1, 2), (2, 1), (3, 0), (0, 4) \qquad \text{Equation 50}$$

The transformation for (m,n)=(0,2), (2,0), (1,3), (3,1), respectively, is two successive reflections shown above. The transformation matrix in this case is $$\begin{pmatrix} 1 & 0 \\ 0 & 1 \end{pmatrix}\begin{pmatrix} 0 & -1 \\ -1 & 0 \end{pmatrix} = \begin{pmatrix} -1 & 0 \\ 0 & -1 \end{pmatrix}$$

and $$\theta_m - \theta_n - n(-1)^n, (m,n) = (0,2), (2,0), (1,3), (3,1) \qquad \text{Equation 51}$$

Combining the conditions of Equations 44, 45 and 46, we arrive at:

$$\theta_m = \theta_n + \frac{\pi}{2}(n-m)(-1)^{n+m} \qquad \text{Equation 52}$$

which suggests $$\xi_i^m = \xi_i^n + (n-m)(-1)^{\xi_1^n + \xi_1^m} \qquad \text{Equation 53}$$

where $\xi^m{}_i \in \theta_m$ and $\xi^n{}_{ii} \in \theta_n$. The mapped orientations of the direction sets, $\theta_1$, $\theta_2$, $\theta_3$ from $\theta_0$ are as follows:

$$\theta_1 = (2,2,2,2,1,1,1,1,1,0,0,3,3,3,1,2,2,3,0,0,0,0,1,1,1) \qquad \text{Equation 54}$$

$$\theta_2 = (1,1,1,1,2,2,2,2,2,3,3,0,0,0,2,1,1,0,3,3,3,3,2,2,2) \qquad \text{Equation 55}$$

$$\theta_3 = (0,0,0,0,3,3,3,3,3,2,2,1,1,1,3,0,0,1,2,2,2,2,3,3,3) \qquad \text{Equation 56}$$

These four orientations are shown in FIG. 22. The smaller boxes represent the nested fractals with their individual orientations.

Two fractals of particular orientation can be connected to form a continuous line by a unique link. The direction of a link between $\xi_i$ and $\xi_j$ is given by $d(\xi_i, \xi_j)$, $$d(\xi_i, \xi_j) = \frac{3 - \left(1 - 2\left[\frac{\xi_i}{2}\right]\right)|2\xi_i - 3|}{2} \qquad \text{Equation 57}$$

where represents the integral part of the fraction. This directional link is shown by the arrows between the boxes in FIG. 21b. The directional link is essential for the physical connectivity of the scan.

In accordance with the present invention, a marked increase in the efficiency of the fault detection algorithm has been obtained by using fractal scanning. The increase in performance is as follows: (1) fractal scanning reduces both the amount of data and the calculation effort; (2) for a scale factor of 2, data is immediately reduced to one-half; (3) as an example, detection of an edge in a 2-D image using a Sobel operator requires 9+9=18 multiplications and 2 additions; a similar edge detection that employs a fractal scan requires 3 multiplications and 1 addition; (4) recursive algorithms for a fractal scan results in increased efficiency; and (5) the 1-D data provide information about both the horizontal and the vertical directions.

D. Application of FDI System to Fabric Defect Detection

The FDI system of the present invention will now be discussed in accordance with the preferred embodiment wherein it is incorporated into a textile fabric manufacturing process. The textile industry is driven by the need for quality control and monitoring in all phases of production. One very important step in quality assurance is the detection and identification of defects occurring in woven fabrics. Unfortunately, there is currently no satisfactory on-line fault detection system available and inspections usually are done manually, which is both ineffective and expensive. The system of the present invention preferably is implemented directly on the loom so that time delay between production and control is minimized.

In order to classify and prioritize textile defects, a survey was conducted by collecting data from five major textile fabric producers in Georgia and South Carolina. The defects were rated based on the most common and the most costly defects.

A description of these defects is given below:

Abrasion: sections of fabric that appear abraded.
Blown Pick: broken pick for an air jet loom.
Bow: where filling yarns lie in an arc across the width of the fabric.
Broken End: where a warp yarn has often ruptured and been repaired; often produced by some mechanical means like chafing; often characterized by the broken end being woven into the fabric.
Broken Pick: where a filling break leaves a pick missing for a portion of the width of the fabric; often caused by weak yarn; often serious enough to cause degrading of woven fabrics.
Coarse End: an end whose diameter is noticeably greater than what is normal to the fabric.

Coarse Pick: a pick of filling whose diameter is noticeably larger than what is normal to the fabric.

Coarse Yarn: a yarn whose diameter is noticeably larger than what is normal to the fabric (may be warp or filling yarn).

Cockled Yarn: a yarn in which some fibers appear wild or tightly curled and disoriented. This is the result of some fibers being too long for the draft roll settings so that the succeeding roll grips the fiber before the preceding roll releases it, causing the fiber to snap and curl. Often appears as tiny slubs in the fabric.

Double End: two ends where only one is called for by the design of the fabric.

Double Pick: two picks in a single shed where only one is called for in the design of the fabric.

Doubling: a filling yarn twice the normal size due to two ends of a roving running together into a single end of spinning. The same occurrence in warp yarn would result in a course end. Two warps weave as one due to faulty drawing in when warp was drawn through harness prior to weaving or due to improper harness action.

End Out: a missing warp yarn; can be due to lack of strength or to breaking.

Filling Band: a visually perceptible band across the width of the fabric directly attributed to a difference in the chemical or physical characteristic of the filling.

Filling Waste: small bunches of waste of whatever was added to the filling yarns to help provide proper tension to yarns.

Flat/Reed Misdraw/Wrong Draw: a misdraw in a plain weave resulting in two ends weaving as one and opposing two other ends weaving as one.

Float: a thread extending unbound over or under threads of the opposite yarn system with which it should have been interlaced.

Fuzz Balls/Lint Balls: balls of fiber encircling the warp yarn formed by the abrasion of the loom. These usually result from the lack of sufficient sizing material on the warp yarns, causing what is generally referred to as soft warp.

Gout: an accumulation of short fiber or fly spun into the yarn or drawn into the loom shed. This defect differs from slubs in that slubs generally are symmetrical in shape while gout appears as undrafted lumps.

Hang Thread: a thread left hanging on the face of the fabric. The most common cause is the failure of a weaver to clip the excess yarn after repairing a broken end and the cloth inspector's failure to remove excess yarn.

Hard Size: a place in a fabric characterized by a harsh, stiff hand and a cloudy, uneven appearance. This is most common in mill finished yarn dyes and is the result of a slasher stop that allows excessive amounts of sizing material to harden onto the yarn. This generally appears in bands across the width of the fabric. Also caused by differences in tension or slight variations of original yarns.

Harness Balk/Harness Skip: an isolated failure of a loom harness to move in its prescribed sequence, causing a filling to float over certain warp ends with which it should have interlaced.

Harness Drop/Harness Breakdown: a place where a harness ceases to function resulting in the ends drawn through that harness floating on the face or on the back of the fabric. Also can give a dotted line appearance from the inner edges of the selvage.

Harness Misdraw: where one or more ends are drawn through the harness contrary to the design of the weave.

Kinky Filling: a place in the fabric where a pick of filling has been given enough slack to twist on itself for a short distance caused by a malfunctioning filling fork, excessive twist in the yarn, inadequate setting of filling twist.

Knot: a place where two ends of yarn have been tied together.

Loom Waste: a place in the fabric where accumulated waste off the loom has found its way into the fabric perhaps by air current.

Loop in Shed: loopy filing, a filling hanging for an instant of time on a warp knot or other protrusion until freed by the stroke of the reed. This results in a short loop of filling appearing on the face of the fabric or kinky filling, a place in a fabric where a filling has been given enough slack to twist on itself for a short distance. Probable causes are a malfunctioning of filling fork, too much power in the picking motion, excessive twist in yarn, inadequate setting of filling twist.

Loopy Filling/Hang Pick: a pick of filling hanging for a split second on a warp knot or other protrusion until freed by the stroke of the reed. This results in a short loop of filling appearing on the face of the fabric.

Mat-up: a place where the warp yarns have become entangled so as to disrupt the proper interlacing of warp and filling caused by loom failing to stop when an end breaks or the introduction of a piece of wild yarns; can be severe.

Mismatch/Mispick: where the weave design is broken by the absence of a pick or a filling.

Mixed Yarn: yarn that is alien to a fabric because of its peculiar chemical or physical characteristics, can be caused by variation in blend or twist.

Neppiness: an excessive amount of tangled mass of fiber appearing on the face of the fabric.

Oily End: a warp yarn that has been soiled by grease or dirt.

Oily Filling: filling yarn that has been soiled by grease and dirt.

Oily Spots: a discolored place or stain on a fabric, resulting from any number of sources.

Reed Mark: a defect resulting from a bent reed wire, characterized by a fine line thin place in the warp direction.

Reedy: a condition characterized by open streaks following the pattern of the reed wires. This can be the result of too coarse reed, wrong reed draw arrangement or improper setting of the loom.

Short Pick: this is the result of the filling insertion mechanism on a shuttleless loom not holding and releasing the filling yarn too soon. This allows the yarn to snap into the body, leaving a missing pick part-way across the width of the fabric. The released pick is then woven into the fabric in a somewhat tangled mass.

Skew: where the filling yarns are off square to the warp ends.

Slack End: the result of a loose or broken end puckering as it is gradually woven into the fabric.

Slack Warp: fabric woven with less than the required tension. Extremes result in an overall crimped or cockled appearance and a stretchy unstable fabric.

Slasher Oil: Like oily spot, but caused by slasher oil.

Sloughed Filling: a defect caused by extra winds of filling slipping from the bobbin and being woven into the fabric. This is usually the result of soft bobbins wound with insufficient tension or too much power on the picker stick of the loom.

Slubby Filling: a bobbin of filling containing numerous slubs (a term used to describe a short thick place in a yarn).

Slub: a term used to describe a short thick place in a yarn that is usually symmetric.

Start Mark: a mark resulting from the warp yarn elongating under tension while a loom is stopped; when the loom is restarted, the slackness is taken up by the weave, leaving a distortion across the width of the fabric.

Stop Mark: a defect resulting from the warp yarn elongating under tension while a loom is stopped; when it is started again, the slackness is taken up by the weave, leaving the distortion across the width of the fabric.

Temple Bruise: a streak along the edge of the fabric that has been scuffed and distorted by a damaged malfunctioning or poorly set temple.

Thick Place: a place across the width containing more picks or heavier filling than that normal to the fabric.

Thin Place: a place across the width containing less picks or lighter filling than that normal to the fabric.

Tight End: an end running taut due to some abnormal restriction. It tends to force the filling to the surface of the fabric and is characterized by a fine line streak of filling showing through like a reed mark.

Uneven Fabric Width: inconsistent fabric width.

Uneven Filling: a filling whose variation of diameter is noticeable enough to detract from the appearance of a fabric caused by choke on a drafting roll, poor distribution of fiber length, less than optimum draft distribution, incorrect roll settings, eccentric behavior of drafting rolls.

Wavy Cloth: cloth woven under conditions of varying tensions, preventing the even placement of filling picks resulting in a fabric with randomly alternating thick and thin places which is generally traceable to a faulty take up motion or let off motion in the loom.

FIG. 22 illustrates a preferred embodiment wherein the FDI system of the present invention is incorporated into an actual loom for detecting and identifying defects of the type defined above in textile fabrics being manufactured. It will be apparent to those skilled in the art that the FDI system of the present invention can be disposed at virtually any location along the loom provided that the location is suitable for capturing an image of the textile fabric being manufactured. In accordance with the preferred embodiment, one CCD array camera 23 is fixedly mounted to a frame 21 every 12 to 15 inches of fabric width. The frame 21 is connected to the loom such that the cameras 23 are disposed to capture images of the fabric 20 being manufactured by the loom. A light source 28 is preferably, but not necessarily, positioned so that the fabric being manufactured is interposed between the light source 28 and the cameras 23. The fabric is moved along the loom by fabric motion motor 27 which receives control signals from fabric motion drive control 26. A computer 29 is coupled to the cameras 23 and to the loom control system (not shown) for obtaining images captured by the cameras 23 and for performing the fractal scanning technique and the WNN analysis of the present invention to detect and identify defects in the fabric 20. The computer 29 controls the manufacturing process in accordance with the types of defects identified to eliminate or minimize defects. The computer 29 preferably contains a Pentium™ processor, but may also contain other types of microprocessors as well as parallel processors. The computer 29 preferably is equipped with a frame grabber card for receiving and storing digital representations of the images captured by each of the cameras 23 in memory inside computer 29. The computer 29 multiplexes among the outputs of cameras 23 so that each of the images captured by each of the cameras 23 is separately analyzed. Each camera 23 looks at one particular area of the fabric 20 so that the combination of the images captured by the cameras 23 make up a full image of the fabric 20. If defects are detected over corresponding scan lines in at least two cameras, the FDI system of the present invention determines that a defect has occurred and proceeds to identify the type of defect.

In accordance with the preferred embodiment, the CCD array cameras 23 are operating in the visible spectrum. The light source 28 preferably comprises four standard fluorescent light bulbs. A diffuser (not shown) disposed between the light source 28 and the fabric 20 provides uniformity in the light being projected on the fabric 20. A television monitor (not shown) can also be coupled to the cameras 23 so that an operator can view the images being captured by the cameras 23. The intensity of the light source 28 can be adjusted by the operator to optimize the images being captured by the cameras 23. A diffuser is chosen based on the type of fabric being inspected to obtain optimum illumination. Also, the portion of the loom proximate the FDI system of the present invention is preferably within an enclosure so that the lighting of the FDI system is closely controlled and noise from other light sources is eliminated or minimized.

In accordance with the preferred embodiment, the CCD array cameras preferably are Polaris Industries Model VT 90D industrial quality high resolution black and white CCD cameras. The Model VT 90D has a resolution of 811 (H)×508 (V) pixels and an image area of 7.95 mm×6.45 mm. The horizontal frequency is 15.734 kHz and the vertical frequency is 60 kHz. The television monitor preferably is a Toshiba monochrome black and white Model TVM 1001 with a 10 inch screen. The frame grabber preferably is a Microdisc, Inc. monochrome frame grabber, Model OC-TCXO-MXD10.

Figure 23:
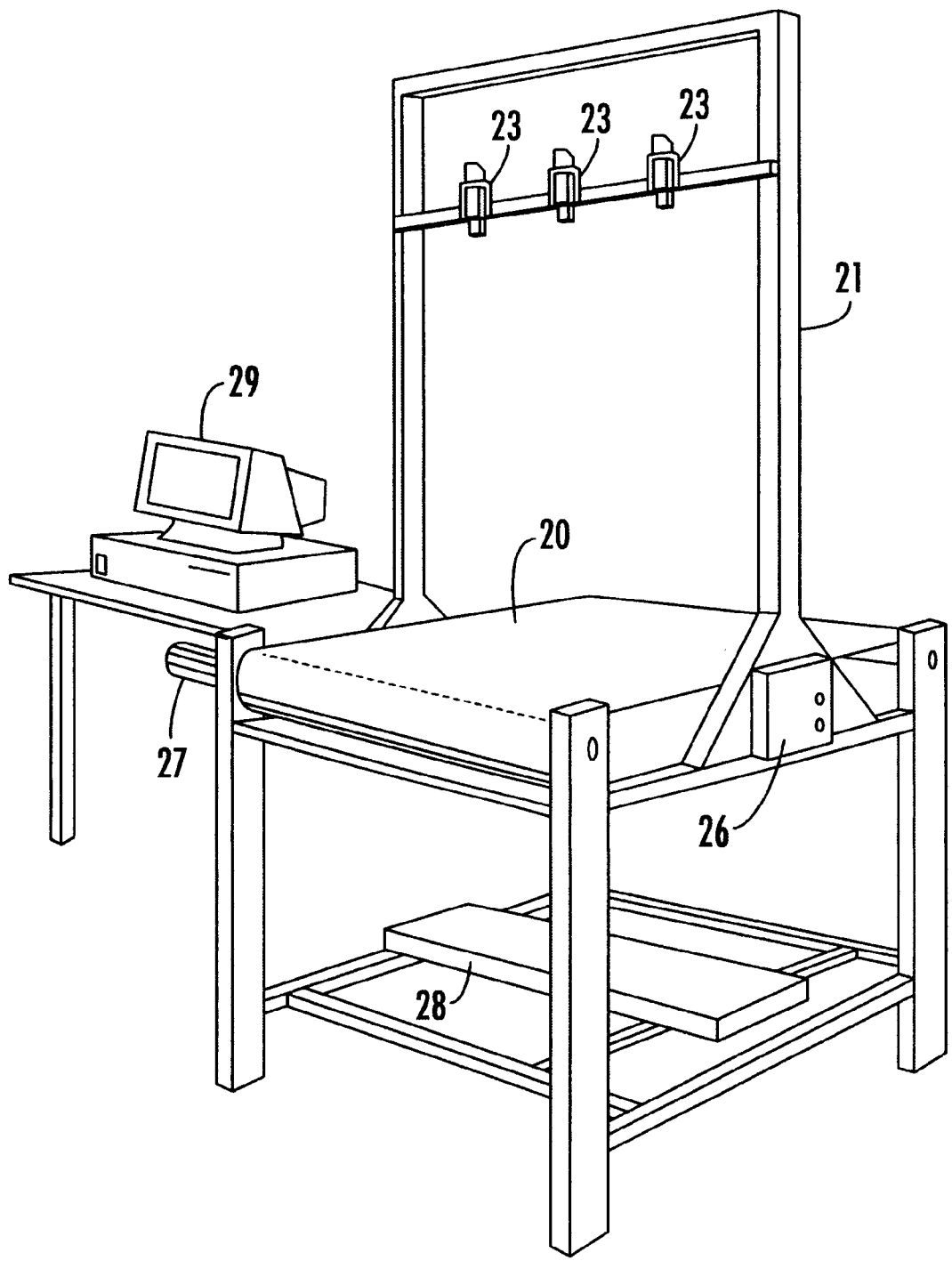
FIG. 23 is a preferred embodiment of the FDI system of the present invention for detecting defects in textile fabrics.

FIG. 23 is an alternative embodiment of the present invention wherein the image sensor 23 is a line scan camera preferably comprising 7,000 pixels arranged in one line, preferably transverse to the movement of the fabric 20. Therefore, only one line of pixels is being used to scan the image. In order to construct a 2-D image with the line scan camera, several lines must be accumulated. However, by accumulating the line scans to build the full image, a higher resolution image is obtained due to the higher resolution of the line scan camera as compared to the CCD array cameras. Once the full image has been obtained, the image is processed to detect and identify defects in the fabric. The processing of the image obtained in accordance with the embodiment of FIG. 16 is essentially the same as the processing of the image obtained in accordance with the embodiment of FIG. 22, with the exception that the frame grabber is unnecessary in the embodiment of FIG. 23.

Figure 24:
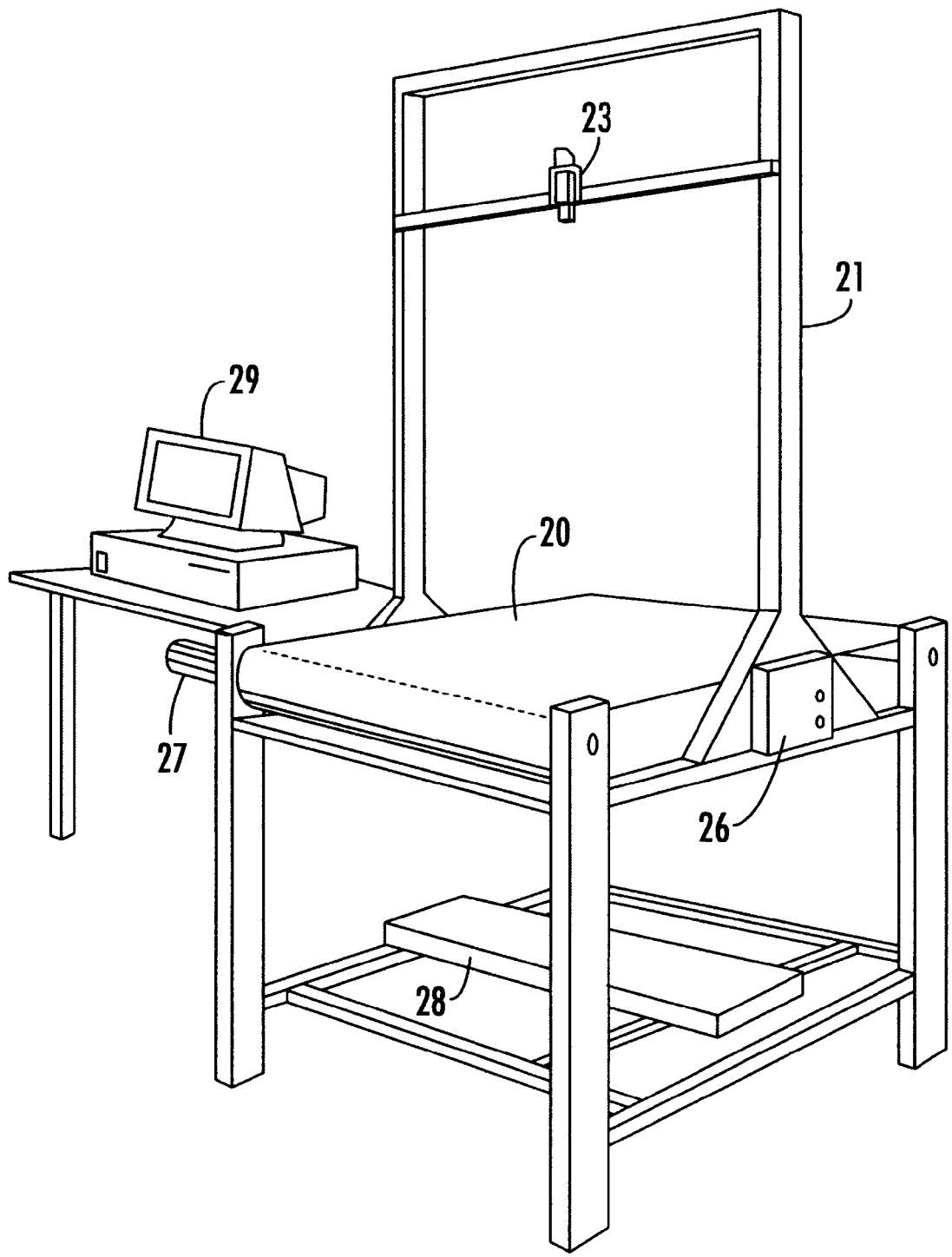
FIG. 24 is an alternative embodiment of the FDI system of the present invention for detecting defects in textile fabrics.
Figure 25:
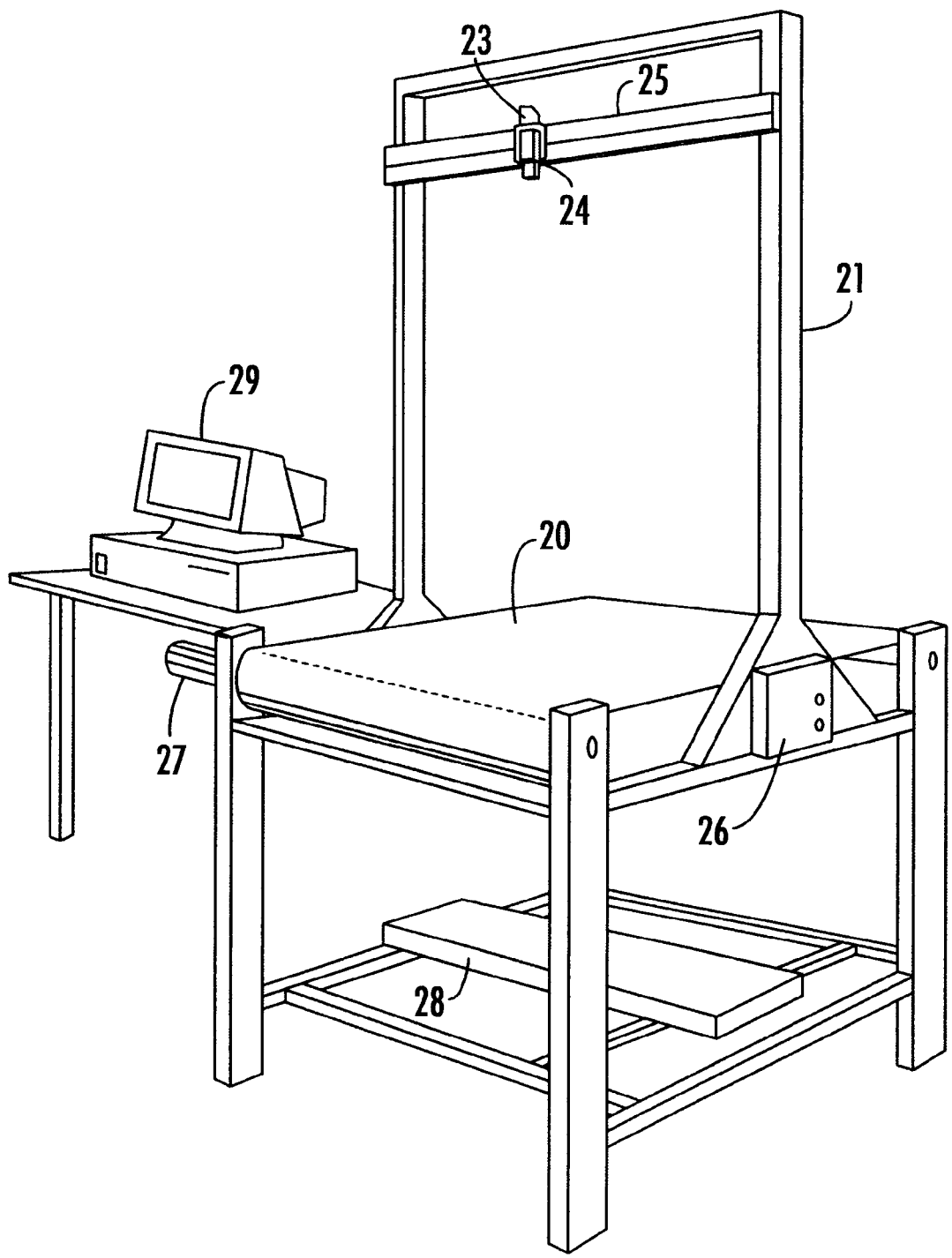
FIG. 25 is an alternative embodiment of the FDI system of the present invention for detecting defects in textile fabrics.

FIG. 24 illustrates another embodiment of the present invention wherein the sensor array 23 is a CCD array camera movably secured to a linear drive 25 via a linear drive stepper motor 24. A stepper motor controller (not shown) is connected to computer 29 and to stepper motor 24 for receiving control signals from computer 29 and for delivering pulses to stepper motor 24 for moving CCD array camera 23 in the longitudinal direction along linear drive 25. A linear slide end-of-travel switch (not shown) is located at each end of linear drive 25 for communicating with computer 29 to enable computer 29 to determine the location of CCD array camera 23 along the linear drive 25. A fabric travel encoder (not shown) comprised in the fabric motion drive control 26 communicates with computer 29 to enable the computer 29 to determine the coordinates of the area of the fabric 20 being captured by CCD array camera 23. In all other respects, the embodiment of FIG. 24 is identical to the embodiments of FIGS. 22 and 23.

The loom incorporates the FDI system of FIG. 17 in order to identify and classify defects, when and if they arise in the process.

Figure 26:
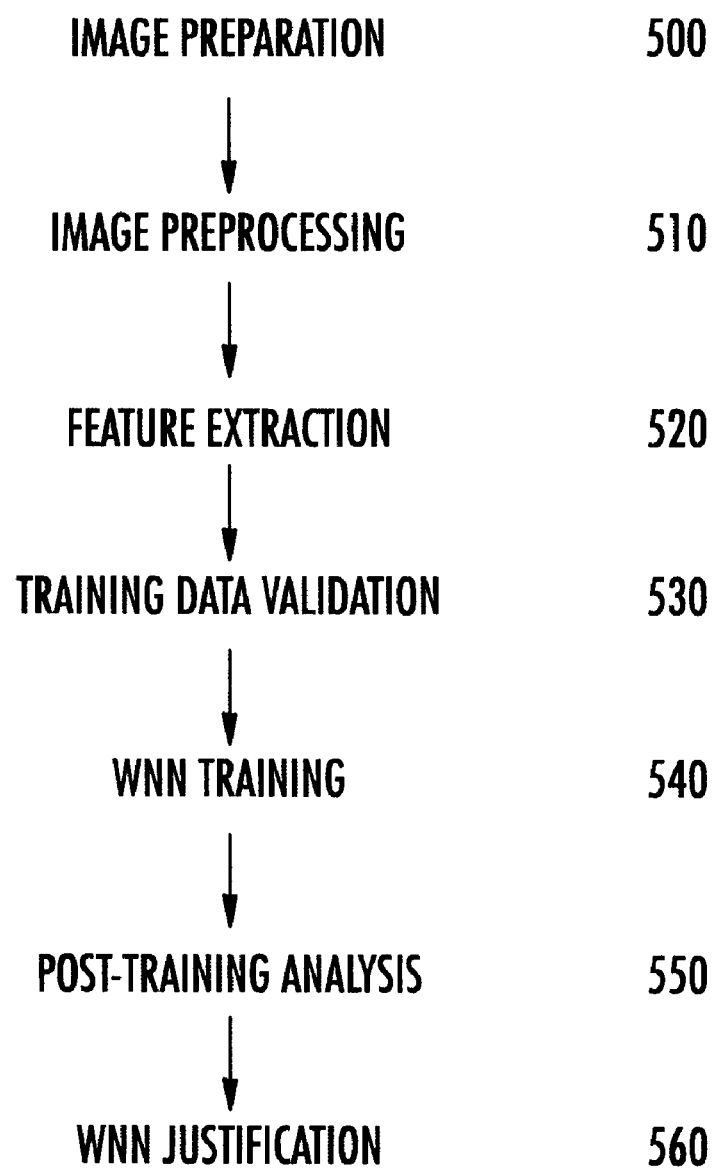
FIG. 26 depicts the process of training an FDI system according to the present invention.

In order to properly operate the system of FIGS. 22–24 it must be trained so that it can recognize the defects that it images. This is done by altering the wavelets so that their activation magnitudes and bandwidths are such that the proper signals (relating to the defect that the node is designed to recognize) activate the node while improper defects (either other defects or no defect) do not activate the node. This is done using the training scheme discussed with respect to sections A-1 and A-3. Further in real world environments the training scheme as FIG. 26. The first step is that of image preparation 500. At this step a number of products containing each potential defect are collected in order to train the system to detect and then classify each defect. The next step image preprocessing 510, the products are imaged and then preprocessed by the preprocessing modules of the pattern recognition system. At this step a number of 1-D signals are prepared and filter to remove the noise components of the signal. Next at feature extraction step 520 a number of features are extracted. The extracted features may either be predetermined using the knowledge of the system designers or by utilizing correlation algorithms for the 1-D signals. Next at the training data validation step 530 the correlated defect information for each type of defect for the selected features is obtained. Next at WNN training step 540 the correlated signals are used to vary the parameters of the WNN as described in sections 3.3.1, 3.2 and 3.3. Next the output of the WNN is reviewed for accuracy to review the convergence of the results for each defect at the post training analysis step 550. The post training analysis step 550 involves a qualitative review by the system designer to determine whether the convergence of the WNN results is in an acceptable range for the specific application of the FDI system. Next the results of the WNN are justified at justification step 560. In this step a number of additional objects with differing predetermined defects are input to the FDI system and the accuracy of the detection and classification system is determined.

Although the embodiments discussed above preferably utilize a light source which produces visible light, it will be apparent to those skilled in the art that other frequencies of light which are not in the visible spectrum can also be used. For example, cameras are available which operate in the infrared spectrum. By using infrared light instead of visible light, some sources of noise can be eliminated so that placing the FDI system in an enclosure may be unnecessary. It is also possible to use other frequencies of light to analyze only the texture of the fabric rather than the color. For example, where the fabric being inspected contains a printed pattern, it is more beneficial to look at the texture of the fabric rather than the color. In this case, it is desirable to use a frequency of light, or a range of frequencies of light, which allow the color of the fabric to be ignored. Therefore, the present invention is not limited to using any particular frequency of light. Similarly, the present invention is not limited to using any particular type of image sensor for obtaining an image of the fabric or to any particular physical arrangement for disposing the image sensor in proximity to the fabric for reading the image. It will be apparent to those skilled in the art that virtually any type of image sensor, light source and means for locating the image sensor and light source along the loom can be used as long as a satisfactory image of the fabric being inspected can be obtained. Furthermore, the present invention is not limited to inspecting any particular types of fabric or to any particular type of fabric manufacturing process. For example, the FDI system of the present invention is suitable for inspection of griege fabrics, and fabrics manufactured by other methods, such as warp knitting, circular knitting, etc.

Although the present invention has been described with respect to particular embodiments, it should be apparent to those skilled in the art that the present invention is not limited to those embodiments. For example, scanning algorithms other than the preferred algorithm discussed above may be suitable for use with the FDI system of the present invention. It will also be apparent to those skilled in the art that, although the preferred transform is the wavelet transform, other types of transforms, such as, for example, the Fourier Transform, can also be used with the FDI system of the present invention depending on the range of frequencies over which the defects are expected to occur, and depending on whether the signal is stationary or non stationary. It is desirable to use the wavelet transform or some other type of transform which provides an analysis which is localized in both the frequency and time domains where the defects are occurring over a wide range of frequencies or where the input signal is non-stationary. The wavelet transform merely is the preferred transform because it is localized in both frequency and time. It should also be clear that the FDI system of the present invention is not limited to detecting defects in textile fabrics but that it may also be used for detecting and identifying other types of defects in other types of products or materials, e.g., paper, glass, food, metals, lumber, etc.

What is claimed is:

1. An apparatus for analyzing a 2-D representation of an object, said apparatus comprising:
    at least one sensor disposed to capture a 2-D representation of at least a portion of an object;
    a memory that stores at least a portion of said 2-D representation received from said sensor;
    a processor containing a program module operative to:
        receive said stored portion of said 2-D representation;
        derive a plurality of features from said stored portion of said representation;
        provide said features to a multi-dimensional wavelet neural network, said multi-dimensional wavelet neural network incorporating a learning technique from the following group consisting of structure learning, parameter learning, or combined parameter and structure learning for classification performance, wherein said features are compared to a predetermined fault pattern to determine if the features represent a defect; and
        produce a classification output indicative of whether said stored portion of said representation comprises a defect; and
    a decision logic unit which receives said features and said classification output and determines if comparing said features to said predetermined fault patterns results in a classification output which is potentially indicative of a predetermined fault pattern, wherein said decision logic unit resolves said classification output by referencing said multi-dimensional wavelet neural network to provide a final declaration as to whether the classification output should be classified as a defect.

2. An apparatus according to claim 1 wherein said at least one sensor comprises a CCD array camera that captures said 2-D representation.

3. An apparatus according to claim 1 further comprising a light source that produces signals having a frequency in either the infared or visible range and wherein said at least one sensor comprises a vision camera responsive to said signals in the infared or visible frequency range.

4. An apparatus according to claim 3 further comprising a light diffuser disposed between said light source and said object for controlling the uniformity and intensity of the signals being projected onto the object.

5. An apparatus according to claim 1 comprising an analog to digital converter that converts said 2-D representation to a digital representation and provides said digital representation to said memory, and wherein said processor derives said at least one signal from said digital representation.

6. An apparatus according to claim 1 wherein said processor derives said at least one signal by projecting said 2-D representation into a 1-D signal.

7. An apparatus according to claim 6 wherein said processor derives said 1-D signal from said 2-D representation by utilizing a projection from the group consisting of vertical scanning, horizontal scanning and fractal scanning.

8. An apparatus according to claim 6 wherein said processor generates some of said features by deriving values from said 1-D signal.

9. An apparatus according to claim 6 wherein said processor generates a feature vector by storing said feature values in an array.

10. An apparatus according to claim 1 wherein said processor determines whether at least one of said features is within a range indicative of a predetermined fault pattern and does not provide said features to said multi-dimensional wavelet neural network if said at least one feature is not within said range.

11. An apparatus according to claim 1 further comprising a decision logic module that receives said classification output from said multi-dimensional wavelet neural network and said features to determine the degree of certainty that said pattern recognition system determines that said predetermined pattern was detected.

12. An apparatus according to claim 1 wherein the object is textile fabric being manufactured by warp knitting.

13. An apparatus according to claim 1 wherein the object is greige fabric.

14. An apparatus according to claim 1 wherein the object is textile fabric being inspected on a device selected from a group consisting of a circular loom, loom, an off-line inspection station or a weaving machine.

15. The apparatus of claim 1, the program module further comprising instructions to provide for a learning element wherein extraction is based on features present in the multi-dimensional wavelet neural network which features are updated based on the resolution of conflicts in the classification output concerning prior derived signals from said logic unit.

16. A method for recognizing defects in an object, comprising:
generating a 2-D digital representation of at least part of an object, the digital representation comprising a plurality of pixels;
extracting a plurality of features from said 2-D digital representation based on classification characteristics;
providing said features to a multi-dimensional wavelet neural network, said multidimensional wavelet neural network incorporating a learning technique from the following group consisting of structure learning, parameter learning, or combined parameter and structure learning for classification performance;
comparing said features to a predetermined fault pattern to determine if the feature represents a defect, and
providing said features and said classification output from said multi-dimensional wavelet neural network to a logic unit to determine if comparing said features to said predetermined fault pattern results in an uncertain classification output, wherein said logic unit resolves uncertainty in said classification output by referencing said multi-dimensional wavelet neural network to determine whether the uncertain classification output should be classified as a defect.

17. A method according to claim 16 wherein said predetermined fault pattern is one of a group of predetermined fault patterns and said multi-dimensional wavelet neural network comprises a plurality of wavelet neurons, wherein the step of providing from said multi-dimensional wavelet neural network comprises a step of determining what classification output to provide by providing an output of said neurons to a competition function, wherein said competition functions provides said classification output.

18. A method according to claim 16 further comprising a step of deriving a 1-D signal from said 2-D representation and wherein the step of extracting a plurality of features from said 2-D digital representation comprises extracting a plurality of features from said 1-D signal.

19. A method according to claim 18 wherein said step of extracting said plurality of features comprises deriving at least one feature of said plurality of features from said 1-D signal.

20. A method according to claim 18 wherein said step of extracting said plurality of features comprises a step convolving said 1-D signal with a plurality of wavelet functions utilizing fast wavelet transforms to produce a plurality of fast wavelet coefficients corresponding to at least one feature of said plurality of features.

21. A method according to claim 18 wherein said step of extracting said plurality of features comprises the steps of:
deriving at least one feature of said plurality of feature values from said 1-D signal;
convolving said 1-D signal with a plurality of wavelet functions utilizing fast wavelet transforms to produce a plurality of wavelet coefficients corresponding to at least one feature of said plurality of features; and
arranging said plurality of features into a feature vector.

22. The method of claim 16 further comprising a step of determining whether at least one of said plurality of features comprise a value indicative of a predetermined pattern, and if said value is not indicative of a predetermined pattern not providing said features to said multi-dimensional wavelet neural network.

23. The method of claim 16 wherein said object comprises a textile material.

24. The method of claim 16, wherein extracting a feature comprises a learning element wherein extraction is based on features present in the multi-dimensional wavelet network which are updated based on the resolution of conflicts in the classification output concerning prior derived signals from said logic unit.

25. A computer readable medium containing instructions for a computer comprising:
means for instructing the computer to read at least a portion of a 2-D digital image, said digital image comprising a plurality of pixels;
means for instructing the computer to generate a feature vector from said digital image based on classification characteristics;
means for instructing the computer to provide said feature vector to a multidimensional wavelet neural network;
means for instructing the computer to provide a classification output indicative of whether said feature vector corresponds to a predetermined pattern; and
means for resolving any conflicts arising from providing such classification output by referencing said multidimensional wavelet neural network to determine which one of a plurality of potentially identified classification outputs should be classified as a defect.

26. The computer readable medium of claim 25 further comprising means for instructing the computer to generate a 1-D representation of said 2-D digital image, wherein said feature vector is generated from said 1-D representation.

27. The computer readable medium of claim 25 wherein said means for instructing the computer to generate a feature vector comprises means for instructing the computer to derive said features from said 1-D signal.

28. A computer readable medium of claim 25 wherein said means for instructing the computer to generate a feature vector comprises means for instructing the computer to convolve said 1-D signal with a plurality of fast wavelet functions.

29. A computer readable medium according to claim 25 further comprising means for instructing said computer to generate a feature library comprising a plurality of selected features, wherein said computer is instructed by said means for instructing the computer to generate said feature vector so that the components of said feature vector each correspond to a value of one of said selected features.

30. A computer readable medium according to claim 25 wherein said multi-dimensional wavelet neural network comprises a plurality of wavelet functions, the computer readable medium further comprising means for instructing said computer to adjust said wavelet functions based upon known feature vectors of said predetermined patterns.

31. A computer readable medium according to claim 25 further comprising means for instructing the computer to determine whether said feature vector comprise at least one value indicative of a predetermined pattern, and if said at least one value is not indicative of a predetermined pattern instructing said computer not provide said feature vector to said multi-dimensional wavelet neural network.

32. The computer readable medium of claim 25, wherein the means for instructing the computer to generate a feature vector further comprises a learning element wherein extraction is based on features present in the multi-dimensional wavelet network which are updated based on the resolution of conflicts in the classification output concerning prior derived signals from said logic unit.

33. An apparatus for pattern recognition comprising:
an input that receives a 2-D representation of at least part of an object;
a memory that stores at least a portion of said 2-D representation; and
a processor that generates a plurality of feature values representing features of said at least one signal and that provides each of said feature values to a perceptron neural network comprising a plurality of neurons each defined by the function $\psi_{a,b} = \sqrt{\text{diag}(a)}(\text{diag}(a)(x-b))$ where x is a vector comprising said feature values, a is a squashing matrix for the neuron and b is the translation vector for that neuron, said perceptron neural network providing a classification output indicative of whether said representation contains a predetermined pattern.

34. An apparatus according to claim 33 wherein said processor derives at least one 1-D signal from said 2-D representation and said processor derives said features from said at least one 1-D signal.

35. An apparatus according to claim 34 wherein said processor derives said 1-D signal from said 2-D representation by utilizing a projection from the group consisting of vertical scanning, horizontal scanning and fractal scanning.

36. An apparatus according to claim 34 wherein said processor generates some of said features by deriving values from said 1-D signal.

37. An apparatus according to claim 34 wherein said processor generates some of said features by convolving said 1-D signal with a plurality of fast wavelet functions.

38. An apparatus according to claim 34 wherein said processor generates a feature vector by storing said features in an array.

39. An apparatus according to claim 33 wherein said processor determines whether at least one of said features is within a range indicative of a predetermined pattern and does not provide said features to said multi-dimensional wavelet neural network if said at least one feature is not within said range.

40. An apparatus according to claim 33 further comprising decision logic module that receives said classification signal from said perceptron neural network to determine the degree of certainty of the detection of said predetermined pattern.

41. An apparatus according to claim 33 wherein said object comprises a textile fabric.

42. An apparatus for analyzing a 2-D representation of an object, said apparatus comprising
at least one sensor disposed to capture a 2-D representation of at least a portion of an object;
a memory that stores at least a portion of the 2-D representation; and
a processor that derives at least one signal from said 2-D representation that generates a feature representing a characteristic fault signature of at least one signal and that provides said feature to a multi-dimensional wavelet neural network which provides a classification output indicative of whether said representation comprises a predetermined pattern;
wherein said multi-dimensional wavelet neural network comprises a plurality of wavelet neurons each defined by $\psi_{a,b} = \sqrt{\text{diag}(a)}\psi(\text{diag}(a)(x-b))$
where x is a vector comprising said feature, a is a squashing matrix for that neuron and b is the translation vector for that neuron.

* * * * *

UNITED STATES PATENT AND TRADEMARK OFFICE
CERTIFICATE OF CORRECTION

PATENT NO. : 6,650,779 B2  
DATED : November 18, 2003  
INVENTOR(S) : George J. Vachtsevanos et al.

It is certified that error appears in the above-identified patent and that said Letters Patent is hereby corrected as shown below:

<u>Title page,</u>  
Item [75], first inventor's name should read -- George J. Vachtsevanos --

Signed and Sealed this

Second Day of March, 2004

JON W. DUDAS  
*Acting Director of the United States Patent and Trademark Office*